(12) United States Patent
Hori

(10) Patent No.: US 9,631,189 B2
(45) Date of Patent: Apr. 25, 2017

(54) METHOD FOR IMMOBILIZING AND RELEASING MICROORGANISM

(71) Applicant: National University Corporation Nagoya University, Nagoya-shi (JP)

(72) Inventor: Katsutoshi Hori, Nagoya (JP)

(73) Assignee: NATIONAL UNIVERSITY CORPORATION NAGOYA UNIVERSITY, Nagoya-Shi (JP)

( * ) Notice: Subject to any disclaimer, the term of this patent is extended or adjusted under 35 U.S.C. 154(b) by 0 days.

(21) Appl. No.: 14/779,717

(22) PCT Filed: Mar. 14, 2014

(86) PCT No.: PCT/JP2014/056966
§ 371 (c)(1),
(2) Date: Sep. 24, 2015

(87) PCT Pub. No.: WO2014/156736
PCT Pub. Date: Oct. 2, 2014

(65) Prior Publication Data
US 2016/0046923 A1    Feb. 18, 2016

(30) Foreign Application Priority Data
Mar. 26, 2013  (JP) ................................. 2013-063695

(51) Int. Cl.
| | |
|---|---|
| *C12N 11/00* | (2006.01) |
| *C12N 11/02* | (2006.01) |
| *C12N 11/08* | (2006.01) |
| *C12N 11/14* | (2006.01) |
| *C12N 1/20* | (2006.01) |
| *C07K 14/21* | (2006.01) |

(52) U.S. Cl.
CPC ............ *C12N 11/00* (2013.01); *C07K 14/212* (2013.01); *C12N 1/20* (2013.01); *C12N 11/02* (2013.01); *C12N 11/08* (2013.01); *C12N 11/14* (2013.01)

(58) Field of Classification Search
None
See application file for complete search history.

(56) References Cited

FOREIGN PATENT DOCUMENTS

WO    WO-2009/104281 A1    8/2009

OTHER PUBLICATIONS

Watanabe et al. (Rapid Conversion of Toluene by an Acinetobacter sp. Tol 5 Mutant Showing Monolayer Adsorption to Water-Oil Interface. Journal of Bioscience and Bioengineering vol. 106, No. 3, 226-230. 2008).*

Ishikawa et al. (Evaluation of adhesiveness of Acinetobacter sp. Tol 5 to abiotic surfaces, Journal of Bioscience and Bioengineering, vol. 113 No. 6, 719-725, 2012).*
Masahito Ishikawa et al., "AtaA, a New Member of the Trimeric Autotransporter Adhesins from Acinetobacter sp. Tol 5 Mediating High Adhesiveness to Various Abiotic Surfaces," PLOS ONE, vol. 7, No. 11, Nov. 2012, e48830, pp. 1-12.
Sheng X X et al., "The influence of ionic strength, nutrients and pH on bacterial adhesion to metals," Journal of Colloid and Interface Science, vol. 321, No. 2, May 15, 2008, pp. 256-264.
Supplementary European Search Report dated Jul. 21, 2016, issued for the European patent application No. 14773956.9.
Junter, G.-A. et al., "Immobilized viable microbial cells: from the process to the proteome . . . or the cart before the horse," Biotechnology Advances 22, 2004, pp. 633-658.
Qureshi, N. et al., "Biofilm reactors for industrial bioconversion processes: employing potential of enhanced reaction rates," Microbial Cell Factories, 2005, 4, 24, pp. 1-21.
Li, X. Z. et al., "Enhanced benzaldehyde tolerance in *Zymomonas mobilis* biofilms and the potential of biofilm applications in fine-chemical production," Applied and Environmental Microbiology, vol. 72 No. 2, 2006, pp. 1639-1644.
Gross, R. et al., "Microbial biofilms: new catalysts for maximizing productivity of long-term biotransformations," Biotechnology and Bioengineering, vol. 98, No. 6, 2007, pp. 1123-1134.
Li, X. Z. et al., "Single-species microbial biofilm screening for industrial applications," Appl. Microbiol. Biotechnol., 76, 2007, pp. 1255-1262.
Rosche, B. et al., "Microbial biofilms: a concept for industrial catalysis?," Trends in Biotechnology, 27, (11), 2009, pp. 636-643.
Halan, B. et al., "Biofilms as living catalysts in continuous chemical syntheses," Trends in Biotechnology, vol. 30, No. 9, Sep. 2012, pp. 453-465.
Cheng, K.-C. et al., "Advances in biofilm reactors for production of value-added products," Appl Microbiol Biotechnol, 87, 2010, pp. 445-456.
Ishikawa, M. et al., "AtaA, a new member of the trimeric autotransporter adhesins from *Acinetobacter* sp. Tol 5 mediating high adhesiveness to various abiotic surfaces," PLOS ONE, vol. 7, Issue 11, 2012, e48830, pp. 1-12.
Linke, D. et al., "Trimeric autotransporter adhesins: variable structure, common function," Trends in Microbiology, 2006, vol. 14, No. 6, pp. 264-270.

(Continued)

*Primary Examiner* — Suzanne M Noakes
*Assistant Examiner* — Jae W Lee
(74) *Attorney, Agent, or Firm* — Locke Lord LLP; James E. Armstrong, IV; Nicholas R. Herrel

(57) ABSTRACT

Intended is to provide a more practical technique for immobilizing a microorganism using an adhesive protein AtaA derived from *Acinetobacter* sp. Tol 5. Provided is a method for attaching and releasing a microorganism, including (1) a step of contacting a microorganism, into which DNA encoding autotransporter adhesin derived from a microorganism belonging to the genus *Acinetobacter* has been introduced to impart or enhance non-specific adhesiveness, with a carrier under a high ionic strength and thus attaching the microorganism to the carrier; and (2) a step of releasing the microorganism from the carrier by washing under a low ionic strength.

10 Claims, 7 Drawing Sheets

(56) References Cited

OTHER PUBLICATIONS

Proceedings of the 45th Autumn Meeting of SCEJ (The Society of Chemical Engineers, Japan) 2013, p. 67.
Proceedings of the 79th Annual Meeting of SCEJ (The Society of Chemical Engineers, Japan) 2014, p. 319.
International Search Report mailed Jun. 17, 2014, issued for PCT/JP2014/056966.

* cited by examiner

METHOD FOR IMMOBILIZING AND RELEASING MICROORGANISM

TECHNICAL FIELD

The present invention relates to a technique for immobilizing microorganisms, and specifically to a method for attaching and releasing a microorganism having adhesiveness (a method including adhesion to a carrier and subsequent release). The present application claims priority based on Japanese Patent Application No. 2013-063695 filed on Mar. 26, 2013, and the content of the patent application is hereby incorporated by reference herein in its entirety.

BACKGROUND ART

Biocatalysts such as enzymes and microbial cells are useful for the production of fine chemicals, general-purpose chemicals, medical intermediates, and biofuels. Biocatalysts catalyze efficient and highly selective reaction under mild conditions such as normal temperature, normal pressure, and neutral conditions. However, bioprocess using biocatalysts requires high production costs, and this problem hinders its commercialization.

Immobilization of biocatalysts has been considered as an important strategy for the cost reduction of bioprocess, because it allows use of the catalyst in repeated and/or continuous reactions, simplifies recovery and isolation of the catalyst and product from the reactor, facilitates the regeneration of the catalyst, and allows the increase in the catalyst concentration per volume. In addition, the use of the whole cell catalyst using the whole of microbial cells markedly contributes to the cost reduction of bioprocess, because, for example, it dispenses with the isolation and purification of the enzyme, it has higher stability than a separated enzyme, it can be proliferated and reactivated, and it does not require the feeding of reducing power such as expensive NADH from the outside. Recently, problems such as restriction of the substance transportation speed and disorders in the cell surface layer, which are the major problems of the use of the whole cell, are being resolved by the development of the technique for surface display localizing the enzyme on the surface of microbial cells.

Prior art techniques for immobilizing microbial cells include entrapment in gel matrix, crosslinking, covalent bonding to a solid surface, and physical adsorption. The used gel, which has been most frequently used, has problems such as the restriction of the substance transportation speed in the gel, cell leakage from the gel, and fragility of the gel. The crosslinking and covalent bonding have problems such as inhibition by the crosslinking agent, and inactivation of cells by the bonding itself. The physical adsorption does not have sufficient adhesiveness for effectively immobilizing general microbial cells, and is only effective for some filamentous fungi. Recently, methodologies for using biofilm as a natural immobilization method are reported (Non-Patent Documents 1 to 8), but there is no method other than screening of the microorganism having the biofilm forming capacity and desired reaction activity, and versatility of the type of microorganisms and reactions is low. In addition, the method is not efficient because it depends on naturally formed biofilm, and is not on the level applicable to actual substance production. Accordingly, prior art immobilization methods are not truly effective, and have many problems, so that the development of a general-purpose and effective immobilization method has been desired.

*Acinetobacter* sp. Tol 5 (*Acinetobacter* sp. Bacterium, Tol 5 strain), which was isolated from a biofilter by the inventors, is a nonpathogenic gram negative bacterium which has high autoagglutinating properties of cells, and shows high adhesiveness to various material surfaces such as various hydrophobic plastic carriers and hydrophilic glass and metal surfaces. As a factor giving such adhesive properties which is not reported for other microorganisms, novel bacterionanofiber existing on the bacterial cell surface layer was discovered, and a new protein composing the nanofiber was identified. This protein belongs to the trimeric autotransporter adhesin (TAA) family, and the present inventors named it AtaA (Non-Patent Document 9). TAA is known as a pathogenic factor included in various gram-negative pathogenic bacteria for specifically adhering to the host cells and extracellular matrix such as collagen, fibronectin, and laminin, thereby infecting the host (Non-Patent Document 10). The protein belonging to the TAA family forms a homotrimer, and builds a common whole structure of head-stoke-membrane anchor domain from the amino terminal toward the carboxyl terminal. However, there are small to large single peptide chains having about 300 to over 3000 amino acid residues, and the amino acid sequences are diversified. The peptide chain of AtaA found by the inventors is composed of 3630 amino acids, and is one of the largest TAAs. It has a unique primary structure composed of a plurality of long repeated sequences arranged in a mosaic pattern on a long stoke. Only the AtaA exhibits nonspecific and high adhesiveness to various surfaces. In addition, the study of TAA focuses on pathogenic bacteria, and there is no study on TAA regarding nonpathogenic bacteria such as Tol 5. On the basis of the results of these studies, the inventors reported the method for imparting or enhancing non-specific adhesiveness and/or autoagglutination to the target microorganism through the introduction of the gene encoding AtaA (Patent Document 1). In Patent Document 1, AtaA and the gene encoding AtaA (ataA gene) were referred to as AadA and aadA gene, respectively.

CITATIONS LIST

Patent Document

Patent Document 1: WO No. 2009/104281

Non-Patent Documents

[Non-Patent Document 1] Junter, G. A.; Jouenne, T., Immobilized viable microbial cells: from the process to the proteome . . . or the cart before the horse. Biotechnol. Adv. 2004, 22, (8), 633-658.

[Non-Patent Document 2] Qureshi, N.; Annous, B. A.; Ezeji, T. C.; Karcher, P.; Maddox, I. S., Biofilm reactors for industrial bioconversion processes: employing potential of enhanced reaction rates. Microb. Cell. Fact. 2005, 4, 24.

[Non-Patent Document 3] Li, X. Z.; Webb, J. S.; Kjelleberg, S.; Rosche, B., Enhanced benzaldehyde tolerance in *Zymomonas mobilis* biofilms and the potential of biofilm applications in fine-chemical production. Applied and Environmental Microbiology 2006, 72, (2), 1639-1644.

[Non-Patent Document 4] Gross, R.; Hauer, B.; Otto, K.; Schmid, A., Microbial biofilms: new catalysts for maximizing productivity of long-term biotransformations. Biotechnology and Bioengineering 2007, 98, (6), 1123-1134.

[Non-Patent Document 5] Li, X. Z.; Hauer, B.; Rosche, B., Single-species microbial biofilm screening for industrial applications. Appl. Microbiol. Biotechnol. 2007, 76, (6), 1255-1262.

[Non-Patent Document 6] Rosche, B.; Li, X. Z.; Hauer, B.; Schmid, A.; Buehler, K., Microbial biofilms: a concept for industrial catalysis? Trends Biotechnol 2009, 27, (11), 636-43.

[Non-Patent Document 7] Halan, B.; Buehler, K.; Schmid, A., Biofilms as living catalysts in continuous chemical syntheses. Trends Biotechnol 2012, 30, (9), 453-65.

[Non-Patent Document 8] Cheng, K. C.; Demirci, A.; Catchmark, J. M., Advances in biofilm reactors for production of value-added products. Appl Microbiol Biotechnol 2010, 87, (2), 445-56.

[Non-Patent Document 9] Ishikawa, M.; Nakatani, H.; Hori, K., AtaA, a new member of the trimeric autotransporter adhesins from *Acinetobacter* sp. Tol 5 mediating high adhesiveness to various abiotic surfaces. PLoS One 2012, 7, (11), e48830.

[Non-Patent Document 10] Linke, D.; Riess, T.; Autenrieth, I. B.; Lupas, A.; Kempf, V. A., Trimeric autotransporter adhesins: variable structure, common function. Trends Microbiol. 2006, 14, (6), 264-270.

SUMMARY OF INVENTION

Technical Problems

As described above, the inventors have invented a novel method for immobilizing a microorganism using AtaA which shows unique adhesive properties and has a relatively simple structure (Patent Document 1). More specifically, they have succeeded in the addition of adhesiveness and autoagglutination through the introduction of the ataA gene into a microorganism having no adhesiveness or autoagglutination. This method is one of the physical adsorption methods, but the adhesiveness is based on the high adhesiveness of AtaA, so that high immobilizing power far higher than the prior art method is exhibited. In addition, the introduction and expression of the ataA gene allows adding adhesiveness to various microorganisms, so that the versatility is high. Furthermore, different from the biofilm through the matrix such as an extracellular polysaccharide and gel-entrapment method, the cells are directly immobilized on the surface through the cell surface protein, so that there is no problem of limitation of the substance transportation speed in the matrix. The material and shape of the carrier may be freely designed. It is a unique, effective, and versatile method for immobilizing a microorganism.

The method reported by the inventors (Patent Document 1) is a highly useful technique which allows immobilization of industrially useful microorganisms, and AtaA used therein has the potential of solving various problems with prior art immobilization techniques. Accordingly, the present invention is intended to provide a more useful immobilization technique, thereby promoting the utilization and application of AtaA which had been found and identified by the present inventors.

Solutions to Problems

As described above, previous studies have revealed that AtaA imparts adhesiveness and/or autoagglutination to the target microorganism. However, details about the adhesion mechanism of AtaA have not been revealed. Therefore, the present inventors studied the adhesive properties of AtaA in detail. In the course of the study, an amazing phenomenon was observed; the AtaA nanofiber cut out and separated from the Tol 5 cell surface adheres to the material surface in the presence of a salt, but cannot adhere in pure water. On the basis of the discussion of this phenomenon, it was assumed that the adhesiveness of AtaA to microbial cells is dependent on the ionic strength, and various validation experiments were carried out. As a result of this, it was revealed that the adhesiveness of the target microorganism, to which AtaA was introduced and expressed, is dependent on the ionic strength. It was also revealed that the change of the ionic strength allows the control of adhesiveness of the target microorganism, and repeated attaching and releasing (adhesion and release) of the target microorganism for the carrier (release while keeping adhesion capacity). Furthermore, it was shown that the catalyst function of the microorganism, to which adhesion capacity is imparted, will not decrease even after repeated attaching and releasing.

The invention described below is mainly based on the above-described findings and results.

[1] A method for attaching and releasing a microorganism including the steps (1) and (2):

(1) a step of contacting a microorganism, into which DNA encoding autotransporter adhesin derived from a microorganism belonging to the genus *Acinetobacter* has been introduced to impart or enhance non-specific adhesiveness, with a carrier under a high ionic strength and thus attaching the microorganism to the carrier; and (2) a step of releasing the microorganism from the carrier by washing under a low ionic strength.

[2] The method of [1], wherein the DNA is an ataA gene.

[3] The method of [1], wherein the DNA is any of the DNA of (a), (b) or (c):

(a) DNA composed of the base sequence of SEQ ID NO. 1;

(b) DNA composed of the base sequence having 90% or more homology with the base sequence of SEQ ID NO. 1, and encoding the protein having activity of imparting or enhancing non-specific adhesiveness to a microorganism;

(c) DNA composed of a part of the base sequence of SEQ ID NO. 1, and encoding the protein having activity of imparting or enhancing non-specific adhesiveness to a microorganism.

[4] The method of [3], wherein the DNA of the following (a) or (b) is introduced into the microorganism together with the DNA encoding an autotransporter adhesin:

(a) DNA composed of the base sequence of SEQ ID NO. 3;

(b) DNA composed of the base sequence having 90% or more homology with the base sequence of SEQ ID NO. 3.

[5] The method of [1], wherein the DNA of the following (a) or (b) including the above-described DNA has been introduced into the microorganism:

(a) DNA composed of the base sequence of SEQ ID NO. 5;

(b) DNA composed of the base sequence having 90% or more homology with the base sequence of SEQ ID NO. 5., and having activity of imparting or enhancing non-specific adhesiveness to a microorganism;

[6] The method of any one of [1] to [5], wherein the boundary ionic strength between the high and low ionic strengths is from 5 mM to 20 mM.

[7] The method of any one of [1] to [5], wherein the boundary ionic strength between the high and low ionic strengths is about 10 mM.

[8] The method of [7], wherein the high ionic strength is from 10 mM to 500 mM, and the low ionic strength is less than 10 mM.

[9] The method of [8], wherein the high ionic strength is from 20 mM to 200 mM.

[10] The method of any one of [1] to [9], wherein the following step (3-1) is carried out after the step (2):

(3-1) a step of recovering the released microorganism.

[11] The method of any one of [1] to [9], wherein the following step (3-2) is carried out after the step (2):

(3-2) a step of recovering the carrier.

[12] The method of any one of [1] to [11], wherein the following step (i) is carried out between the steps (1) and (2):

(i) a step of contacting the microorganism attached to the carrier with a liquid to be treated, and keeping the contact state.

[13] The method of [12], wherein the microorganism has capacity of producing a specific enzyme, and the liquid to be treated comprises the substrate of the enzyme.

[14] The method of any one of [1] to [13], wherein the microorganism is a microorganism belonging to the genus *Escherichia*.

DESCRIPTION OF EMBODIMENTS

Figure 1:
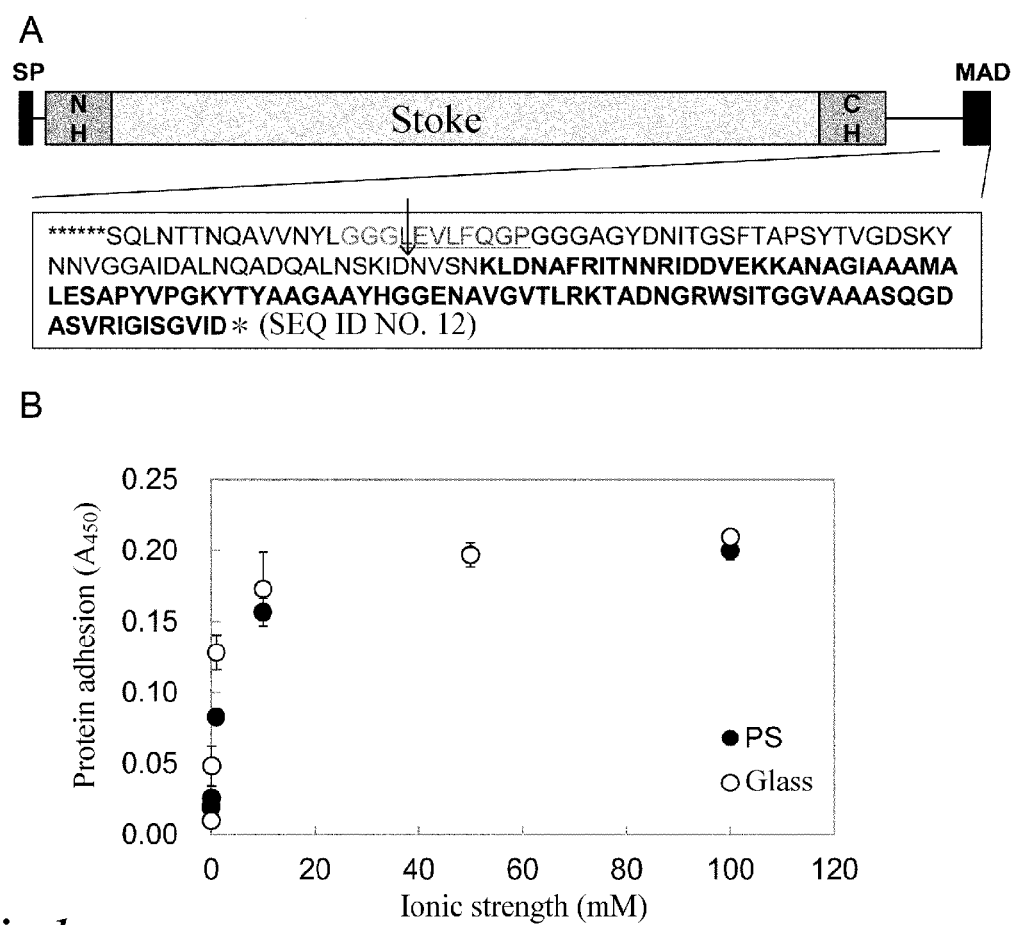
FIG. 1 shows the design of 3CataA and the ionic strength dependence of adhesion to a polystyrene (PS) plate and a glass plate. (A) 3CAtaA was designed in such a manner that the recognition sequence of HRV 3C protease and a glycine linker of three residues are inserted into the point near the root of the region exposed at the surface of AtaA. The amino acid sequence near the carboxyl terminal of the designed protein is shown. The amino acid region composing the outer membrane binding domain (MAD) is represented in boldface type. The recognition sequence of HRV 3C protease is underlined. The three amino acid residues immediately before the sequence are the glycine linker (GGG). The arrow indicates the protease cleavage site. NH and CH in the schematic view show the amino-terminal head domain, and the head domain near the carboxyl terminal, respectively. In addition, SP is signal peptide, and does not exist in the AtaA fiber exposed at the cell surface layer. (B) The relationship between the adhesiveness of the purified 3CAtaA to a PS plate and a glass plate and the ionic strength was studied by ELISA. The result is expressed in average±standard error (n=3).

The present invention relates to the method for attaching and releasing a microorganism using an autotransporter adhesin derived from a microorganism belonging to the genus *Acinetobacter*. In the present invention, "the attaching and releasing method" means the method including a step (operation) of attaching a microorganism to a carrier, and a step (operation) of releasing the microorganism from the carrier.

Autotransporter adhesins are proteins reported as adhesive nanofibers expressed by gram-negative bacteria, and are known to specifically interact with the tissues, cell surface molecules, and extracellular matrix of the host. Autotransporter adhesins are said to have functions such as adhesion, invasion, cytotoxicity, blood serum resistance, and intercellular propagation. Autotransporter adhesins have a common architecture including N-terminal signal peptide, internal passenger domain, and C-terminal translocator domain. Among them, the C-terminal translocator domain defines this protein family. Secretion of an autotransporter adhesin is initiated by a signal peptide, and starts from the passage through the inner membrane by the Sec system. Subsequently, the translocator domain is inserted into the outer membrane, and forms a β barrel structure. Finally, the passenger domain passes through the tunnel formed with the barrel, and appears on the surface of the bacterial cells. Autotransporter adhesins are classified into monomeric autotransporter adhesins and trimeric autotransporter adhesins (Shane E. Cotter, Neeraj K. Surana and Joseph W. St Geme III 2005. Trimeric autotransporters: a distinct subfamily of Autotransporter proteins. TRENDS in Microbiology. 13: 199-205). The translocator domain of a monomeric autotransporter adhesin is considered to form a β barrel structure composed of 12 transmembrane antiparallel β sheets by one subunit. However the translocator domain of a trimeric autotransporter adhesin is known to form a trimer which is stable to heat and resistant to SDS in the outer membrane, and the subunit having four β sheets is oligomerized to form a 12-strand β barrel structure by three subunits. Furthermore, actually the passenger domain of all the monomeric autotransporter adhesins is linked to the bacteria surface in the translocator domain through a noncovalent bond, or released extracellularly. On the other hand, for all the trimeric autotransporter adhesin proteins, the passenger domain likely remains to be linked to the translocator domain through a covalent bond.

The trimeric autotransporter adhesin is abbreviated as TAA (trimeric autotransporter adhesin), and also referred to as Oca family (Oligomeric Coiled-coil Adhesin Family) which is a new class forming a coiled coil having a common oligomer structure (Andreas Roggenkamp, Nikolaus Ackermann, Christoph A. Jacobi, Konrad Truelzsch, Harald Hoffmann, and Jurgen Heesemann 2003. Molecular analysis of transport and oligomerization of the *Yersinia enterocolitica* adhesin YadA. J Bacteriol. 185: 3735-3744).

As shown by the below-described examples, the attaching and releasing method of the present invention is based on the surprising finding that the adhesiveness of the trimeric autotransporter adhesin AtaA derived from the *Acinetobacter* sp. Tol5 strain depends on the ionic strength, and includes the following steps (1) and (2):

(1) a step of contacting a microorganism, into which DNA encoding autotransporter adhesin derived from a microorganism belonging to the genus *Acinetobacter* has been introduced to impart or enhance non-specific adhesiveness, with a carrier under a high ionic strength and thus attaching the microorganism to the carrier; and (2) a step of releasing the microorganism from the carrier by washing under a low ionic strength.

In the step (1), more specifically the adhesion step, firstly, a microorganism, into which DNA encoding TAA derived from a microorganism belonging to the genus *Acinetobacter* (adhesiveness-imparting DNA) has been introduced to impart or enhance non-specific adhesiveness (hereinafter referred to as "adhesiveness-imparted microorganism") is provided.

The adhesiveness-imparting DNA is preferably the ataA gene isolated and identified from the *Acinetobacter* sp. Tol5 strain. The ataA gene is composed of the base sequence represented by SEQ ID NO. 1, and encodes the protein AtaA represented by SEQ ID NO. 2. The *Acinetobacter* sp. Tol5 strain has capacity of degrading toluene and was isolated from the exhaust gas treating reactor, and deposited to International Patent Organism Depositary, National Institute of Technology and Evaluation (NITE IPOD) under the accession number FERM P-17188 (Tsukuba Center Chuo No. 6, 1-1-1 Higashi Tsukuba-shi, Ibaraki, Japan).

In one preferred embodiment, the DNA composed of the base sequence represented by SEQ ID NO. 1 is used as the adhesiveness-imparting DNA, or its equivalent in terms of function may be used. Examples of the DNA which is functionally equivalent to the DNA composed of the base sequence represented by SEQ ID NO. 1 include the DNA which is composed of the base sequence having 70% or more, preferably 80% or more, more preferably 90% or more, even more preferably 95% or more, most preferably 98% or more homology (or identity) with the base sequence represented by SEQ ID NO. 1, and encodes the protein having activity of imparting or enhancing non-specific adhesiveness to a microorganism. Another example is the DNA which hybridizes with the DNA composed of the base sequence complementary to the base sequence represented by SEQ ID NO. 1 under stringent conditions, and encodes the protein having activity of imparting or enhancing non-specific adhesiveness to a microorganism. Yet another example is the DNA which is composed of a part of the base sequence represented by SEQ ID NO. 1, and encodes the protein having activity of imparting or enhancing non-specific adhesiveness to a microorganism, in other words, the DNA of the deleted gene composed of the base sequence prepared by deleting several tens to several thousands of continuous base sequences from the base sequence represented by SEQ ID NO. 1 at one or more points, and the protein translated by it will not lose its activity of imparting or enhancing non-specific adhesiveness.

Stringent conditions mean the conditions which form a specific hybrid and no nonspecific hybrid, and examples thereof include low and high stringent conditions, but are preferably high stringent conditions. The low stringent conditions mean, for example, the conditions including washing after hybridization at 42° C., 5×SSC, 0.1% SDS, preferably at 50° C., 5×SSC, 0.1% SDS. The high stringent conditions mean, for example, the conditions including washing after hybridization at 65° C., 0.1×SSC and 0.1% SDS.

The mutation in the base sequence preferably keeps the domain structure composed of a signal peptide, a head domain, a neck domain, a stoke domain, and a membrane anchor domain. In the base sequence represented by SEQ ID NO. 1, the signal peptide corresponds to the bases of the positions 1 to 171, the head domain corresponds to the bases of the positions 322 to 807 and 8989 to 9444, the neck domain corresponds to the bases of the positions 886 to 957 and 9445 to 9516, the stoke domain corresponds to the bases of the positions 1216 to 8898 and 9517 to 10611, and the membrane anchor domain corresponds to the bases of the positions 10612 to 10890.

In the DNA composed of a part of the base sequence represented by SEQ ID NO. 1, the several tens to several thousands of continuous base sequences which can be deleted are preferably the sequence region encoding one or both stoke domains, one head domain, and one neck domain, and one or a plurality of continuous sequences may be deleted. It is more preferred that the region (the positions 322 to 8898) encoding the whole region from the head domain close to the amino terminal to the stoke domain, or the region (the position 8989 to 10611) encoding the whole region from the head domain close to the carboxy terminal to the stoke domain be deleted from the above-described each domains. It is even more preferred that a plurality of repeated regions found in the coding region of the stoke domain be deleted in such a manner that they each appear once without repetition. It is most preferred that any one of the plurality of repeated regions which is found in the coding region of the stoke domain.

The non-specific adhesiveness of the target microorganism is further improved by introducing the DNA composed of the base sequence represented by SEQ ID NO. 3 into the target microorganism, together with the DNA encoding the autotransporter adhesin. A gene functionally equivalent to the DNA composed of the base sequence represented by SEQ ID NO. 3 may be introduced. Examples of the DNA functionally equivalent to the DNA composed of the base sequence represented by SEQ ID NO. 3 include the DNA composed of the base sequence having 90% or more, preferably 95% or more, and more preferably 98% or more homology with the DNA composed of the base sequence represented by SEQ ID NO. 3. Other examples include the DNA which hybridizes with the DNA having a base sequence complementary to the base sequence represented by SEQ ID NO. 3 under stringent conditions. The base sequence represented by SEQ ID NO. 3 is a sequence found immediately below the AtaA gene of the Tol5 strain, and encodes ORF of the protein showing homology with the outer membrane protein ompA gene, BamE gene, and omlA gene included in gram-negative bacteria. Tol5-OmlT (referred to as Tol5-OmpA in Patent Document 1) as the ORF is composed of 264 amino acids (SEQ ID NO. 4) encoded by the 795-bp gene (SEQ ID NO. 3).

The operon containing the DNA encoding the autotransporter adhesin may be introduced to the target microorganism. For example, the introduction of the DNA composed of the base sequence represented by SEQ ID NO. 5 into the target microorganism allows the introduction of the DNA encoding the above-described outer membrane protein to the target microorganism together with the DNA encoding the autotransporter adhesin. Other operon functionally equivalent to the above-described operon may be introduced. Examples of the functionally equivalent operon include the operon composed of the DNA which is composed of a base sequence having 70% or more, preferably 80% or more, more preferably 90% or more, even more preferably 95% or more, most preferably 98% or more homology with the base sequence represented by SEQ ID NO. 5, and has activity of imparting or enhancing non-specific adhesiveness and/or autoagglutination to the host microorganism. The base sequence represented by SEQ ID NO. 5 is the operon (ataA-omLT operon) isolated and identified from the Tol5 strain, and contains the promoter/ribosome bound site (the positions 1 to 106), ataA gene (the positions 107 to 10999) and Tol5-omlT gene (the positions 11064 to 11858). The *E. coli* DH5α transformed by the vector including the operon is deposited as "DH5α-XLTOPO::aadA-ompA to NITE Patent Microorganisms Depositary (NPMD) (2-5-8 Kazusakamatari, Kisarazu-shi, Chiba, Japan) under the accession number NITE BP-490 (date of accession Feb. 19, 2008).

The microorganism (target microorganism) subjected to the introduction of the adhesiveness-imparting DNA may be selected from various microorganisms. The target microorganism is not particularly limited, and examples include the microorganisms having no or weak non-specific adhesiveness. The target microorganism may be wild strain, mutant, or gene recombinant strain. An appropriate microorganism is selected according to the intended use of the present invention. Examples of the target microorganism include a bacterium belonging to the genus *Escherichia* such as *Escherichia coli*, a bacterium belonging to the genus *Acinetobacter* such as *Acinetobacter calcoaceticus*, a bacterium belonging to the genus *Ralstonia* such as *Ralstonia eutropha*, a bacterium belonging to the genus *Pseudomonas* such as *Pseudomonas putida* and *Pseudomonas fluorescens*, a bacterium belonging to the genus *Aeromonas* such as *Aeromonas caviae*, a bacterium belonging to the genus *Alcaligenes* such as *Alcaligenes latus*, a bacterium belonging to the genus *Xanthomonas* such as *Xanthomonas campestris*, a bacterium belonging to the genus *Desulfomonile* such as *Desulfomonile tiedjei*, a bacterium belonging to the genus *Desulfuromonas* such as *Desulfuromonas chloroethenica*, a bacterium belonging to the genus *Chromobacterium* such as *Chromobacterium chocolatum*, a bacterium belonging to the genus *Burkholderia* such as *Burkholderia arboris*, a bacterium belonging to the genus *Rhodobacter*, a bacterium belonging to the genus *Acidovorax* such as *Acidovorax facilis*, and a bacterium belonging to the genus *Zymomonas* such as *Zymomonas mobilis*.

Through the introduction of the adhesiveness-imparting DNA to the target microorganism for transformation, a microorganism having imparted or enhanced non-specific adhesiveness is obtained. Typically, the adhesiveness-imparting DNA is linked to an appropriate vector, and the target microorganism (host microorganism) is transformed by the vector, thereby obtaining a microorganism having imparted or enhanced non-specific adhesiveness. Specifically, the DNA is introduced to the host microorganism by multicopy, or the DNA is linked under control of the promoter which is expressed constitutively, or the DNA is linked under control of an enzyme-inducible promoter, thereby obtaining a microorganism having imparted or enhanced non-specific adhesiveness.

Firstly, the intended DNA is linked to the vector, thereby making a recombinant vector. Phages, cosmids, artificial chromosomes, or plasmids which can autonomously replicate in the host cell are used as the vector. Furthermore, plasmids which are integrated into the chromosome can be used as the expression cassette. In this case, the vector must have autonomous replication capability in the host (for example, *Escherichia coli*) in which the expression cassette is constructed, but the autonomous replication capability is not necessarily required in the host into which the expression cassette is introduced (for example, *Acinetobacter* sp. bacteria). The recombinant vector may be, for example, a shuttle vector designed so as to be useful for both of *Escherichia coli* and the bacterium belonging to the genus *Acinetobacter*.

Examples of the plasmid include the plasmid derived from *Escherichia coli* (for example, pET21a(+), pET32a(+), pET39b(+), pET40b(+), pET43.1a(+), pET44a(+), pKK223-3, pGEX4T, pUC118, pUC119, pUC18, and pUC19), and *Escherichia coli*-*Acinetobacter* shuttle vector plasmid pARP3 (Non-Patent Document 9), and examples of the phage DNA include λ, phage (λ, gt11, λ, ZAP, and the like). Alternatively, a commercially available cloning vector such as pCR4-TOPO (registered trademark) may be used for cloning and sequence confirmation.

Insertion of DNA into a vector is carried out by, for example, cleaving purified DNA with an appropriate restrictive enzyme, inserting it into the restriction site or multicloning site of an appropriate vector DNA, and then linking it to a vector. For example, the intended DNA may be synthesized by a commonly known method, and incorporated into a vector. The DNA may be amplified by the PCR method using a primer so as to contain the sites cleaved by an appropriate restrictive enzyme at each end. The conditions of PCR reaction may be appropriately established by those skilled in the art.

The recombinant vector may be linked to, in addition to the promoter and DNA of the present invention, as necessary, a cis element such as an enhancer, a selected marker, and a ribosome-binding sequence (SD sequence). Examples of the selection marker include, but not limited to, drug-resistant markers such as kanamycin, ampicillin, tetracycline, and chloramphenicol, and auxotrophic markers such as leucine, histidine, lysine, methionine, arginine, tryptophan, and uracil.

The promoter is not particularly limited, and may be appropriately selected by those skilled in the art according to the host microorganism. For example, when the host is *Escherichia coli*, T7 promoter, lac promoter, trp promoter, or λ-PL promoter may be used. A promoter composed of the base sequence represented by SEQ ID NO. 6, and those functionally equivalent to the promoter, such as a promoter composed of the base sequence having 90% or more, preferably 95% or more, more preferably 98% or more homology with the base sequence represented by SEQ ID NO. 6 are also preferred.

Linking of the DNA fragment and vector fragment may use a known DNA ligase. The DNA fragment and vector fragment are linked together after annealing, thereby making a recombinant vector. The recombinant vector can be obtained by ligation reaction under normal conditions preferably using a commercially available ligation kit, such as Ligation High (manufactured by Toyobo Co., Ltd.).

The recombinant DNA technique including cloning, ligation, and PCR may use, for example, those described in Sambrook, J et al., Molecular Cloning 2nd ed., 9. 47-9. 58, Cold Spring Harbor Lab. Press (1989) and Short Protocols In Molecular Biology, Third Edition, A Compendium of Methods from Current Protocols in Molecular Biology, John Wiley & Sons, Inc.

The vector thus obtained may be as necessary purified by, for example, the boiling method, alkali SDS method, magnetic beads method, or a commercially available kit using any of these principles, and followed by, for example, concentration by any concentration means such as the ethanol precipitation method or polyethylene glycol precipitation method.

The method for introducing a recombinant vector into the target microorganism is not particularly limited, and examples thereof include the heat shock method using calcium ions, the electroporation method, and the lipofection method.

The transformed microorganism containing the intended DNA may be screened by forming a colony on an LB medium agar plate containing antibiotics such as ampicillin and kanamycin using the marker gene included in the recombinant vector. In order to check whether the cloned host microorganism is transformed by the recombinant vector, a part of the microorganism may be subjected to the amplification confirmation of insert by the PCR method, or the sequence analysis by the dideoxy method using a sequencer. Other than the method of introducing an autonomously replicable plasmid, an introduction method of chromosome incorporation type may be used, the method including placing a region homologous to the chromosomal gene in the vector, and causing homologous recombination to introduce the target gene.

The method for culturing the transformed microorganism thus obtained in a medium is carried out according to an ordinary method used for culturing the target microorganism. The medium for culturing the transformed microorganism obtained by using a microorganism such as *Escherichia coli* as the host may be a natural or synthetic medium as long as it contains, for example, a carbon source, a nitrogen source, inorganic salts which can be assimilated by the microorganism, and allows efficient culturing of the transformed microorganism. Specific examples include the M9 medium, M9G medium, BS medium, LB medium, Nutrient Broth medium, meat extract medium, SOB medium, and SOC medium.

The carbon source may be a carbon compound which can be assimilated, and examples thereof include saccharides such as glucose, polyols such as glycerin, alcohols such as methanol and ethanol, or organic acids such as pyruvic acid, succinic acid, citric acid, and lactic acid, fatty acids, and oil and fat. The nitrogen source may be a nitrogen compound which can be assimilated, and examples thereof include peptone, meat extract, yeast extract, casein hydrolysate, soybean cake alkali extract, alkylamines such as methylamine, and ammonia or salts thereof. In addition, salts such as phosphates, carbonates, sulfates, magnesium, calcium, potassium, iron, manganese, and zinc, specific amino acids, specific vitamins, and an anti-foaming agent may be used as necessary. Furthermore, a protein expression inducer such as isopropyl-β-D-thiogalactopyranoside may be added to the medium as necessary.

The culturing is usually carried out under aerobic conditions such as shake culture or aeration stirred culture, preferably at 0 to 40° C., more preferably 10 to 37° C., particularly preferably 15 to 37° C. During the culturing period, the medium pH may be changed as appropriate within the range which allows the growth of the host and will not impair activity of the autotransporter adhesin, and is preferably about pH4 to 8. The pH is adjusted using, for example, an inorganic or organic acid, or an alkaline solution. During culturing, as necessary, an antibiotic such as ampicillin or tetracycline may be added to the medium.

As described above, a microorganism having imparted or enhanced non-specific adhesiveness is obtained. The non-specific adhesiveness of the microorganism thus obtained may be evaluated using the adhesion test (CV adhesion test) by crystal violet staining. The specific method is, for example, as follows: the culture broth is subjected to centrifugation, the culture supernatant is removed, an inorganic salt medium containing neither carbon source nor nitrogen source or a salt solution is added to the bacterial cell pellet, a bacterial cell suspension is obtained by ultrasonication, the turbidity $OD_{660}$ of the bacterial cell suspension is adjusted to a constant value (in the vicinity of 0.5) with the medium or the salt solution, the suspension is added to each well of a 96-well polystyrene plate in portions of 200 µl and incubated for 2 hours at a temperature optimum for the microorganism, the suspension in the well is thoroughly removed by a pipette, the well is washed with 200 µl of the inorganic salt medium or the salt solution twice and air-dried, 1% crystal violet aqueous solution is added to the wells and incubated for 15 minutes at room temperature, the crystal violet is removed by a pipette, the wells are washed three times with 200 µl of the inorganic salt medium, the crystal violet is eluted from the attached bacterial cells stained with 70% aqueous ethanol solution, and then the absorbance $A_{590}$ is measured. When the absorbance $A_{590}$ is 0.7 or more, preferably 1.0 or more, more preferably 1.5 or more, the microorganism is regarded as a microorganism having non-specific adhesiveness. The adhesion test may be carried out by any modified method of the above-described method, as long as the method is based on a principle that microbial cells are attached to the inner wall of an appropriate container under non-growth conditions, the attached cells are stained with an appropriate staining agent, and the amount of the attached cells are quantified by quantifying the staining agent or the number of stained cells. For example, the material and volume of the plate, the number of wells, the type and amount of the staining agent and cleaning liquid, the staining time and temperature, the concentration of suspended cells, the apparatus used for quantifying the staining agent and the number of stained cells (for example, spectrophotometer, plate reader, and microscope) may be appropriately selected. The staining agent may be safranine or a fluorescent dye. The adhesiveness may be evaluated by the comparison with a wild strain (negative control) having no adhesiveness-imparting DNA.

In the step (1) of the present invention, the prepared adhesiveness-imparted microorganism is contacted with a carrier under conditions where the adhesive protein, which is an expression product of the adhesiveness-imparting DNA, exhibits adhesiveness, more specifically, under a high ionic strength, thereby attaching the adhesiveness-imparted microorganism to the carrier. The border between the high ionic strength and low ionic strength (the conditions of the below-described step (2)) can be varied by the DNA used for imparting adhesiveness, and may be established by those skilled in the art based on a preliminary experiment with reference to the disclosure of the present description. It is preferred that the ionic strength at which the adhesiveness drastically changes be used as the "border" herein. For example, the border between the high ionic strength and the low ionic strength may be from 5 mM to 20 mM. In this case, the high ionic strength is, for example, from 10 mM to 500 mM, preferably from 20 mM to 200 mM. If a too high ionic strength is used, activity and existence of the adhesiveness-imparted microorganism can be adversely affected. Specific examples of the border include 5 mM, 7 mM, 10 mM, and 15 mM.

The type and constitution of the solution used in the step (1) (solution of high ionic strength) are not specifically limited. For example, various buffer solutions, various salt solutions, and media may be used.

The microorganism used in the present invention shows non-specific adhesiveness, so that various carriers (immobilizing carriers) may be used. The surface properties (for example, hydrophilicity and hydrophobicity), material, and form of the carrier are not particularly limited. Examples of the material include polyethylene, polystyrene, polycarbonate, silicon, nylon, polypropylene, polyvinyl alcohol, urethane, chitosan, cellulose derivatives, glass, ceramic, and metal, and examples of the form include plate, sphere, granules, nonwoven fabric, fiber, film, and sponge (foam).

Two or more adhesiveness-imparted microorganisms may be used in combination. This embodiment is useful when, for example, treatment or reaction is continuously carried out in two or more stages using the adhesiveness-imparted microorganism attached to a carrier, which is obtained by the step (1).

A contact state of the adhesiveness-imparted microorganism and carrier may be formed by dropping or adding a suspension of the adhesiveness-imparted microorganism to the carrier, or put the carrier into a solution containing the adhesiveness-imparted microorganism. This operation is preferably followed by incubation for 1 minute to 3 hours, thereby increasing the rate of adhesion. Alternatively, the adhesiveness-imparted microorganism may be grown in a culture broth containing salts in the presence of the carrier, thereby attaching the microorganism to the carrier simultaneously with growth.

The adhesiveness-imparted microorganism attached to the carrier by the step (1) is usually subjected to one or more treatment or reaction (details about this treatment or reaction will be described below). In the present invention, thereafter, the step (2), more specifically, the release step is carried out. In the step (2), the adhesiveness-imparted microorganism is released from the carrier by washing under a low ionic strength. In the present invention, the release of the adhesiveness-imparted microorganism is carried out by a simple operation of washing under a low ionic strength. This point is one of the greatest features of the present invention, and is advantageous in practicality and versatility.

In the present invention, the border between the high and low ionic strengths is as described above, and the low ionic strength is preferably less than 10 mM (0 mM or more and below 10 mM). The low ionic strength is more preferably 0 mM to 5 mM.

The buffer solution, medium, or the like satisfying the above-described conditions may be used as washing water. In order to achieve more reliable releasing and simple operation, the washing operation preferably uses water substantially free of ions or containing very few ions, more specifically, deionized water, distilled water, pure water, or ultrapure water. For example, the washing operation is carried out by keeping the carrier to which the adhesiveness-imparted microorganism is attached is kept in washing water for a predetermined time (for example, one minute to three hours) (during this time, the washing water may be stirred, and the carrier may be shaken), or washing water is continuously or intermittently sprayed over the carrier to which the adhesiveness-imparted microorganism is attached. The washing water may be replaced by a new one during the washing operation. In addition, the washing operation may be repeated twice or more.

The steps (1) and (2), more specifically the adhesion to the carrier and release may be repeated. In this case, the adhesiveness-imparted microorganism and/or carrier may be replaced with a new one (for example, the same type, similar one, or different one) in midstream.

In one embodiment, after the step (2), the released adhesiveness-imparted microorganism is recovered (step (3-1)). The recovered adhesiveness-imparted microorganism may be reused for the method of the present invention or other purpose. For example, a new carrier is put into the suspension of the adhesiveness-imparted microorganism recovered with the washing water, that is, the suspension of the released adhesiveness-imparted microorganism, and salts are dissolved, thereby attaching (immobilizing) the adhesiveness-imparted microorganism to the carrier. The recovered adhesiveness-imparted microorganism may be reused in such a manner after regeneration.

In another embodiment, after the step (2), the carrier is recovered (step (3-2)). The recovered carrier may be reused for the method of the present invention or other purpose. The recovered carrier may be reused after regeneration or activation. This embodiment is particularly useful when durability of the carrier is high, or the carrier is expensive.

The method of the present invention is applicable to various uses using an immobilized microorganism, such as the production of medicines, medical intermediates, and medical raw materials, the production of pesticides, the production of bioethanol, the production of biodiesel, the synthesis of chemicals, the production of foods (for example, isomerized sugars, maltodextrins, oligosaccharides, synthetic sweeteners, amino acids, peptides, and vitamins), and treatment of sewage, drains, industrial waste liquids, and industrial waste water. Therefore, in one embodiment of the present invention, the following step, more specifically, a step of contacting the adhesiveness-imparted microorganism attached to the carrier with the liquid to be treated, and keeping the contact state (step (i)) is carried out between the steps (1) and (2). The liquid to be treated is selected according to the intended use. For example, when the production or synthesis of a substance accompanied by enzyme reaction (for example, the above-described medicines, bioethanol, biodiesel, chemicals, and food) is carried out, a solution containing the substrate of the enzyme is used as the liquid to be treated. In this case, an adhesiveness-imparted microorganism having capacity of producing the specific enzyme causing the enzyme reaction is used. Examples of the specific enzyme include lipase, protease, peptidase, esterase, cellulase, hemicellulase, α-amylase, β-amylase, β-glucanase, glutaminase, isomerase, dehydrogenase, reductase, peroxidase, kinase, phosphatase, glycosyl transferase, and dechlorination enzymes. The enzyme produced by the adhesiveness-imparted microorganism may be an intracellular enzyme, extracellular enzyme, enzyme localized in the bacterial surface layer, or enzyme displayed at the cell surface.

The step (i) may be carried out using, for example, a continuous reaction vessel/reaction chamber, or batch type reaction vessel/reaction chamber.

EXAMPLES

A. Study of Adhesive Properties of AtaA

In order to advance the utilization and application of AtaA as the trimeric autotransporter adhesin (TAA) derived from *Acinetobacter* sp. Tol 5, the adhesive properties of AtaA were studied in detail.

1. Method and Material (1) Strain and Culture Conditions

The Tol 5 strain and its mutant were cultured at 28° C. in an inorganic salt medium or LB medium containing 0.05% toluene. The *Acinetobacter* sp. bacterium ADP1 strain and its mutant were cultured at 30° C. in an LB medium. The antibiotics were added as necessary at the following concentrations. Ampicillin: 500 μg/mL, gentamycin: 10 μg/mL for Tol 5-derived mutant. Ampicillin: 100 μg/mL, gentamycin 10 μg/mL for ADP1-derived mutant. For inducing the ataA gene, 0.5% arabinose was added.

(2) Construction of p3CAtaA

Using overlap PCR, the whole length of the DNA sequence encoding the HRV3C protease recognition site was inserted into the ataA gene. The first PCR was carried out using the primer set composed of the Bgl II ataA S primer (5'-GGTTTGAGCAATAAAGATCTAAATTCAAC-3': SEQ ID NO. 7) and 3C protease ataA AS primer (5'-GGGTCCCTGAAAGAGGACTTCAAGCCCACCAC-CAAGATAATTGACTAC-3': SEQ ID NO. 8), or the set composed of the XbaI ataA AS primer (5'-TGGGTCTAGA-GAATTAGTCAATCAC-3': SEQ ID NO. 9) and 3C protease ataA S primer (5'-CTTGAAGTCCTCTTTCA-GGGACCCGGTGGTGGGGCAGGTTATGACAAC-3': SEQ ID NO. 10). PrimeSTAR Max DNA polymerase (manufactured by Takara Bio Inc.) was used. Amplification of the DNA fragment of interest from the template plasmid (pTA2-ataA) was confirmed by agarose electrophoresis. Using the amplification product, Bgl II ataA S primer, and XbaI ataA AS primer, the second PCR was carried out. The amplified 3CataA fragment was subcloned into the pTA2 vector (manufactured by Toyobo Co., Ltd.). The vector construct pTA2-3C thus obtained was treated with Bgl II and Xba I, and the generated DNA fragment (containing the C-terminal side head, HRV 3C recognition site, and membrane binding anchor region) was ligated with the pTA2-ataA plasmid, and used as pTA2-3CataA. Finally, the 3CataA gene was subcloned into the pARP3 vector (Non-Patent Document 9), thereby obtained the plasmid p3CataA.

The 4140 strain, which is the ataA gene-deletion mutant of Tol 5, was transformed by conjugation with the donor strain *E. coli* S17-1 (Simon, R.; Priefer, U.; Puhler, A., Bio-Technol 1983, 1, (9), 784-791) that had p3CAtaA.

(3) SDS-PAGE and Immunoblotting

The bacteria cell suspension or protein solution was dissolved in a 2×SDS-PAGE loading solution, and heated at 97° C. for 5 minutes. These samples were isolated by electrophoresis on 7.5% polyacrylamide using a tris-glycine SDS buffer solution, and subjected to CBB staining. In the immunoblotting, the protein isolated by SDS-PAGE was transferred to a PVDF membrane by the semi-dry method. The membrane was subjected to blocking treatment by incubation for one hour in a PBS buffer solution containing 5% skim milk, and reacted with the anti-AtaA antiserum against $AtaA_{699-1014}$ for 1 hour. The membrane was washed with a PBST buffer solution for 10 minutes, and allowed to react with a peroxidase-bound anti-rabbit IgG secondary antibody at room temperature for one hour. The membrane was washed with a PBST buffer solution three times, and the bound antibody was detected with ECL Prime Detection Reagent (GE Healthcare).

(4) Flow Cytometry

The bacteria cell suspension was fixed sequentially in 2% and 4% paraformaldehyde for 10 minutes, and the cells were recovered by centrifugation. The cells were washed with deionized water twice, and then allowed to react with the anti-AtaA antiserum in PBS for 30 minutes. After washing with PBS once, the cells were allowed to react with Alexa Flour 488-bound anti-rabbit IgG secondary antibody in an NET buffer solution. The stained cells were washed with PBS twice, resuspended in deionized water, and analyzed with flow cytometry (FACSCant, BD).

(5) Adhesion Test

The bacterial strain cultured in an LB medium overnight was inoculated in an LB medium in an amount of 1/100, and cultured under shaking at 115 rpm. Tol 5 and its mutant were cultured at 28° C. for 8 hours, and ADP1 and its mutant were cultured at 30° C. for 12 hours. When the ataA gene was induced, 0.5% arabinose was added upon inoculation. After culturing, the bacterial cells were collected by centrifugation, washed three times with deionized water, and suspended again in KCl aqueous solutions at different concentrations. Finally, the cell concentration $OD_{660}$ was adjusted to 0.5, and 200 μl of the suspension was transferred to a 96-well polystyrene (PS) plate or glass plate. The cells were incubated at 28° C. for 2 hours for attaching them thereto, the wells were washed twice with a KCl solution having the same concentration, and the attached cells were stained with 1% crystal violet for 15 minutes. After staining, the wells were washed another three times with a KCl solution having the same concentration, the staining agent was eluted from the cells with 70% ethanol, and quantified by measuring the absorbance at 590 nm.

(6) Release Test

In the same manner as in the adhesion test, a 100 mM KCl suspension of ADP1(pAtaA) cells was prepared. This suspension was added to a 96-well PS plate or glass plate, and incubated at 28° C. for 2 hours thereby attaching the cells thereto. Thereafter, the plate was washed three times with a KCl solution having the same concentration or deionized water, and the remaining cells were stained with 1% crystal violet. Thereafter, the cells were washed with KCl having the same concentration or deionized water, and then the staining agent was quantified in the same manner as in the adhesion test.

(7) Re-Adhesion Test

In the same manner as in the adhesion test, a 100 mM KCl suspension of bacterial cells was prepared. The bacterial cells in the bacterial suspension were attached to a 96-well PS plate in the same manner, and three wells were used for quantification of attached cells. This procedure is the same as in the adhesion test. Other wells were washed three times with deionized water, the bacterial cells released in the cleaning liquid were collected by centrifugation and suspended again in 100 mM KCl, and the $OD_{660}$ was readjusted to 0.5. This cell suspension was used for the re-adhesion test. Thereafter, the same operation was repeated.

(8) Measurement of Esterase Activity

The ADP1(pAtaA) cells were subjected to re-adhesion test by the above-described method. The 96-well plate to which the cells are attached to was washed with 100 mM KCl, and then 200 µl of 4-NBP reaction solution (1.9 mM p-nitrophenyl butyrate, 1.1% triton-X 100, 50 mM 3,3-dimethylglutaric acid, 50 mM tris, 50 mM 2-amino-2-methyl-1,3-propanediol) was added, and incubated for 30 minutes at room temperature. Thereafter, the absorbance at 405 nm, which is the absorption wavelength of paranitrophenol as the product, was measured using a microplate reader, thereby determining esterase activity.

2. Result and Discussion (1) Separation and Purification of AtaA Protein and Analysis of Adhesive Properties In order to cut out AtaA from the cell surface of Tol 5, the recognized sequence of HRV 3C protease (LEVLFQGP: SEQ ID NO. 11) was inserted into the FGG region, which is supposed to form a loop near the outer membrane binding anchor domain (MAD) of AtaA, together with the linker composed of three glycine residues (GGG) (FIG. 1A). This modified ataA gene p3CataA was introduced into the ataA-deficient 4140 strain, thereby obtaining 4140 (p3CAtaA). 3CAtaA was detected from the whole cell lysate, to which ataA expression was induced by arabinose, by Western blotting using the anti-AtaA serum (the result not shown). In addition, the flow cytometry analysis using the same antiserum indicated that 3CAtaA is shown to be displayed on the cell surface (the result not shown). The adhesion test showed that 4140 (p3CAtaA) more strongly adheres to a polystyrene (PS) surface and a glass surface than the Tol 5 cells which constantly express original AtaA (the result not shown).

Subsequently, 3CAtaA was cleaved from the cell surface by HRV 3C protease, and precipitated and isolated by 30% ammonium sulfate. The isolate was subjected to SDS-PAGE and Western blotting, and confirmed to be a monomer of 3CAtaA (the result not shown). Furthermore, the isolate was subjected to Native PAGE, and the protein having a molecular weight of 720 kDa or more was detected (the result not shown). AtaA belonging to the TAA family is supposed to have a homotrimer structure, and the 3CAtaA, which had been actually obtained by cleaving from the vicinity of the outer membrane binding region, followed by isolation and purification, was shown to maintain a polymer structure.

The adhesive properties of the separated and purified 3CAtaA itself to the PS surface and glass surface were studied by ELISA. The influence on adhesion was analyzed with the ionic strength changed by potassium chloride (KCl). 3CAtaA adhered to both the surfaces in the presence of a small amount of ions. However, the adhesiveness drastically decreased at 10 mM or lower, and it hardly adhered to the PS surface or glass surface in pure water containing no ion (FIG. 1B).

(2) Ionic Strength Dependency of Microbial Cell Adhesion by AtaA

Figure 2:
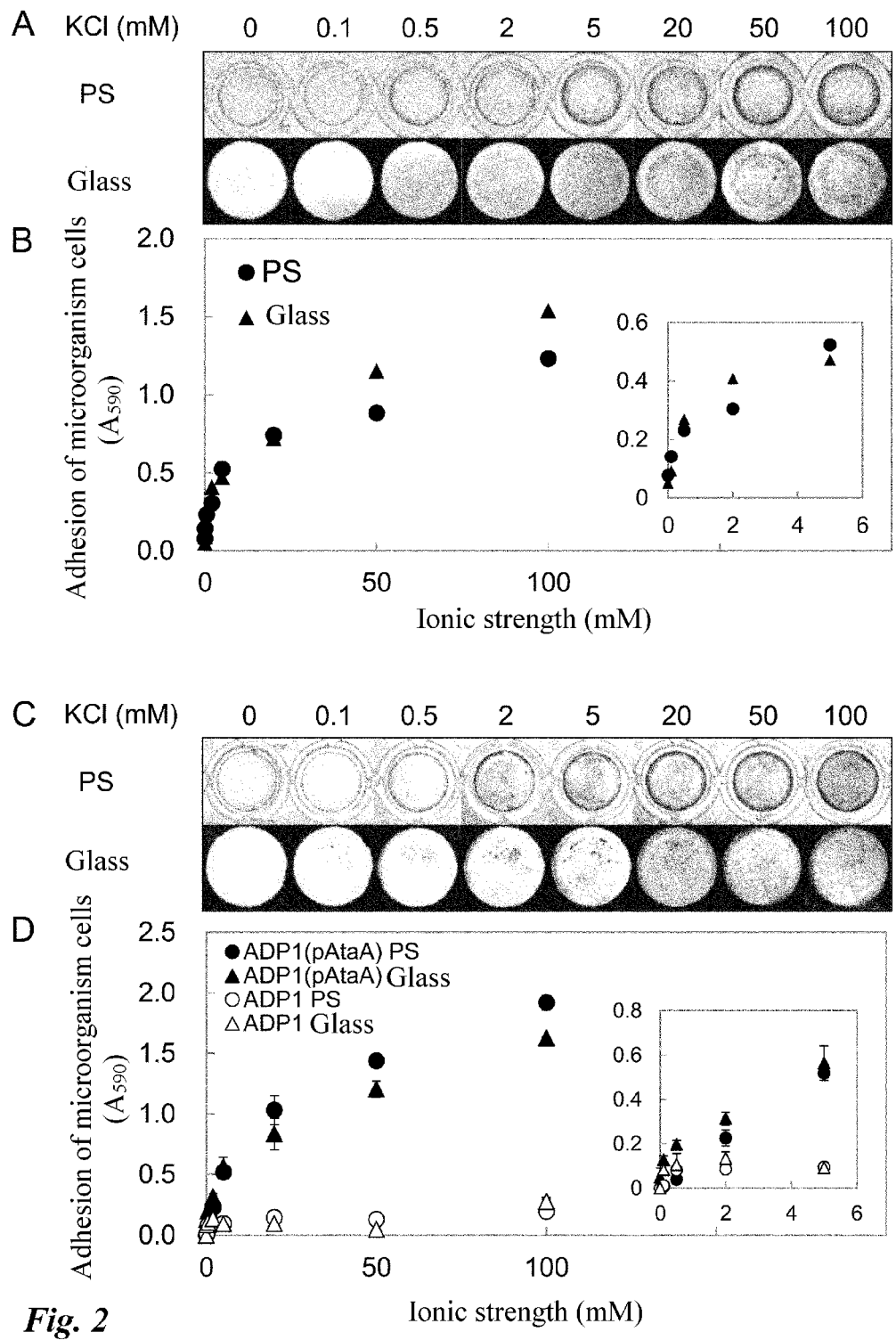
FIG. 2 shows the adhesion of microbial cells through AtaA under various ionic strengths. Using a PS plate and a glass plate, the Tol5 cells, ADP1 cells, and ADP1(pAtaA) cells were incubated in KCl solutions at various concentrations (0 to 100 mM). Thereafter, the attached cells were visualized by crystal violet staining (A: Tol 5, C: ADP1 (pAtaA)). Crystal violet was eluted from the attached cells, and the absorbance at 590 nm ($A_{590}$) was measured, thereby quantifying the attached cells (B: Tol5, D: ADP1(pAtaA) ●, ▲, and ADP1 ○, Δ). The ● and ○ in the graph are the measured values when a PS plate was used, and ▲ and Δ are the measured values when a glass plate was used. The result is shown by the average±standard error obtained from three independent experiments (n=3).

On the basis of the above-described discovery, whether the adhesion of microbial cells by AtaA is influenced by the ionic strength was studied using a Tol 5 wild strain. As a result, it was found that the adhesion of the Tol 5 cells itself is dependent on the ionic strength (FIGS. 2A and 2B). High adhesiveness was exhibited to PS and glass although a slight influence by the ionic strength was observed at 20 mM or more. However, the adhesiveness drastically decreased at 5 mM or less, and the cells hardly adhered to both the surfaces in pure water.

Figure 3:
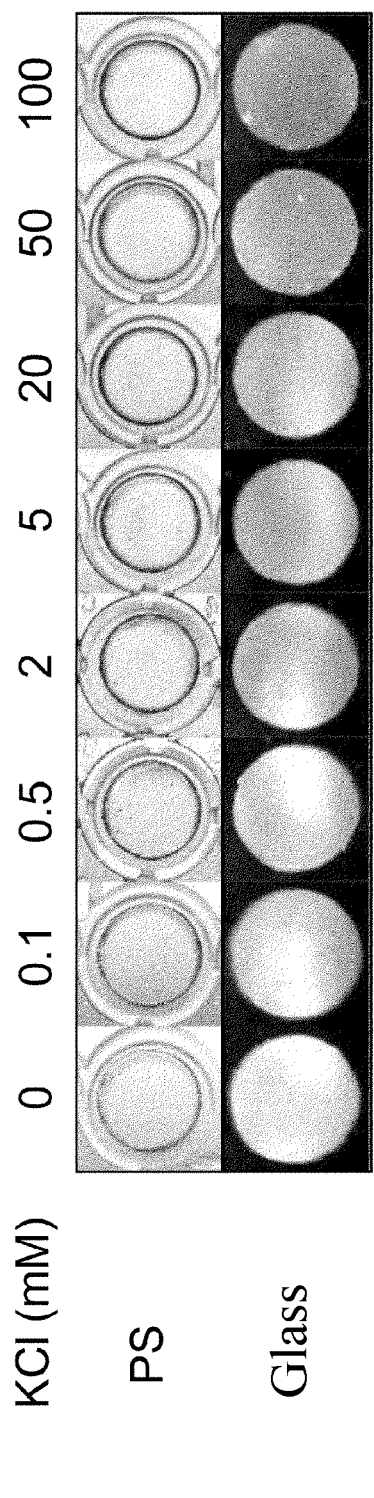
FIG. 3 shows the adhesion of ADP1 cells to a PS plate and a glass plate. The ADP1 cells attached to the PS plate/glass plate were visualized by crystal violet staining.

In order to examine whether the ionic strength dependency of the microbial cell adhesion directly reflects the adhesive properties of AtaA, ADP1 belonging to the genus *Acinetobacter*, which is a different bacterium belonging to the same genus, and ADP1(pAtaA) including the ataA gene were studied for their adhesive properties. It has already reported that ADP1 originally has no adhesiveness or autoagglutination, while ADP1(pAtaA) shows high adhesiveness and autoagglutination (Non-Patent Document 9). This was confirmed also this time. The ADP1 wild strain hardly adhered to the PS surface or glass surface irrespective of the ionic strength (FIGS. 3 and 2D). On the other hand, ADP1(pAtaA) showed higher adhesiveness to both the surfaces with the increase of the ionic strength (FIGS. 2C and 2D). As in the case of Tol 5 cells, the adhesiveness drastically decreased at 5 mM or less, and the cells hardly adhered to both the surfaces in pure water. More specifically, the high adhesiveness given to the ADP1 cells by the introduction of the ataA gene is not exerted in pure water or under a very low ionic strength, and this fact likely reflects the adhesive properties of AtaA, as with the Tol 5 cells. In consideration of the above results, the use of a solution having an ionic strength of 10 mM or more (preferably 20 mM or more) is preferred for attaching a microorganism, to which adhesiveness has been imparted by AtaA, to a carrier, and a solution having an ionic strength of less than 10 mM (preferably 5 mM or less) is preferred for releasing the microorganism from the carrier.

The adhesiveness of general microbial cells is far lower than the adhesiveness by AtaA, and is not at the level useful for immobilizing the microorganism, but is known to show similar ionic strength dependency, and is explained by the DLVO theory. According to this theory, the energy necessary for the approach and attachment of microbial cells to the surface is the total of the energy applied to both of Van der Waals attraction and electrostatic repulsive force, so that the decrease of the ionic strength increases the electrostatic repulsive force, and thus hinders attachment of microbial cells. When the ionic strength is below a certain level, the energy of microorganisms to approach the surface cannot be exceeded by the motile energy or the energy of Brownian motion of microbial cells themselves. Because of this energy barrier, microbial cells cannot directly reach the surface, so they attach to the surface via the extracellular polymer or nanofibers on the cell surface. The radiuses of curvature of the extracellular polymer and nanofiber are far smaller than cells themselves, so that there is no energy barrier. There should be no energy barrier in the adhesion of AtaA as nanofiber, and the loss of adhesion ability in pure water cannot be explained by this theory. However, the ionic strength dependency of the cell adhesion itself is similar to the general microorganism adhesive properties reflecting the DLVO theory. Therefore, in order to confirm whether the surface potentials of ADP1 and ADP1(pAtaA) are different or not, the ionic strength dependencies of the electrophoresis of the cells were compared. As a result, their profiles of the electrophoresis speed completely identical to each other, and the ionic strength dependencies were the same regardless of the presence or absence of AtaA (the result not shown). As described above, for the ADP1 wild strain, the adhesiveness is not improved by the increase of the ionic strength. Therefore, the high adhesiveness of the ADP1(pAtaA) cells in the presence of ions is brought about by AtaA, and the loss of adhesiveness under a low ionic strength and in pure water reflects the adhesive properties of AtaA, so that the difference from the DLVO theory is strongly suggested. In any case, this proves that the microbial cells, to which adhesiveness was imparted by AtaA, hardly adhere in pure water or under an extremely low ionic strength.

(2) Technique for Attaching and Releasing Microorganism Using AtaA

Figure 4:
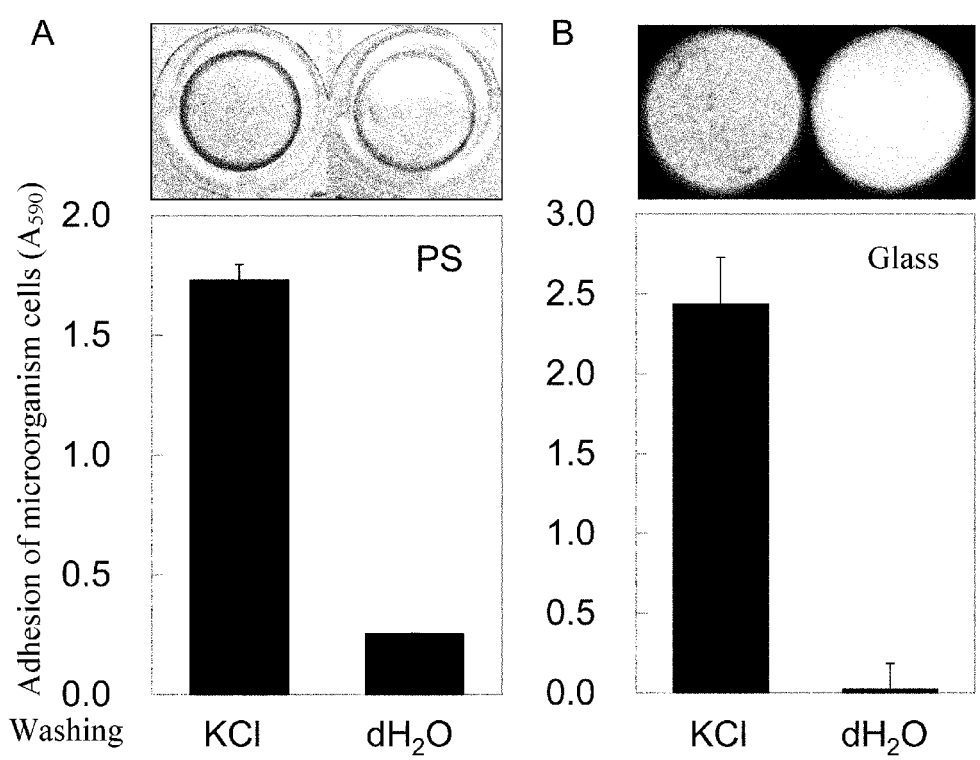
FIG. 4 shows release of the attached ADP1(pAtaA) cells by pure water. Using the PS plate (A) and glass plate (B), the ADP1(pAtaA) cells were incubated in a 100 mM KCl solution. Thereafter, the cells were washed three times with a 100 mM KCl solution or pure water, and the remaining cells were stained with crystal violet for visualization. The staining agent was eluted from the cells, and quantified by measuring the absorbance at 590 nm ($A_{590}$). The result is shown by the average±standard error obtained by the three independent experiments (n=3).
Figure 5:
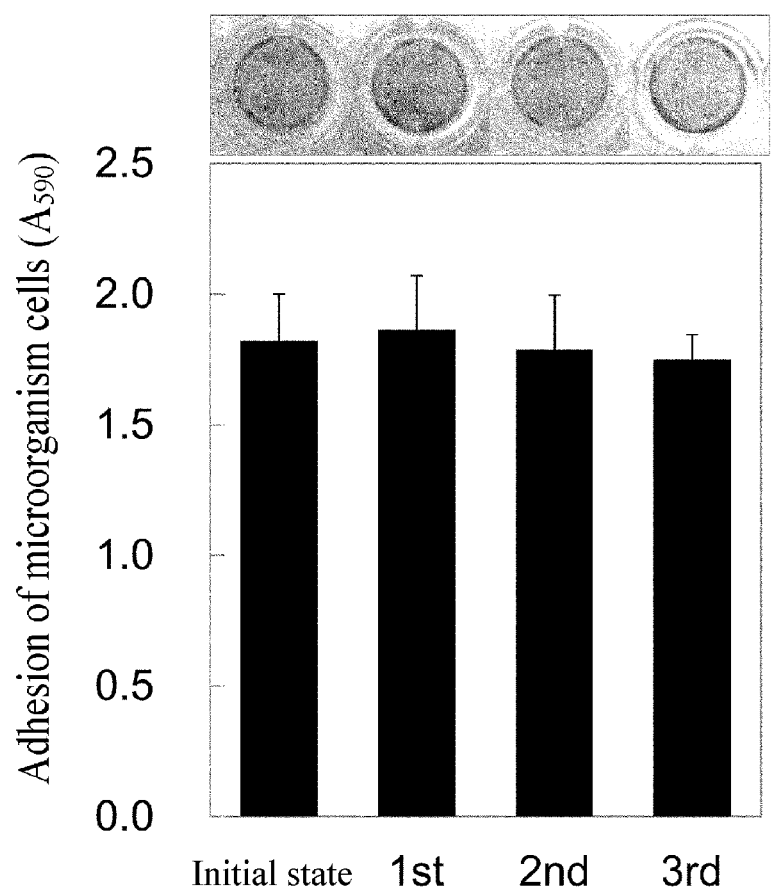
FIG. 5 shows the change of adhesiveness by repletion of attaching and releasing of ADP1(pAtaA) cells. The ADP1 (pAtaA) cells were suspended in a 100 mM KCl solution, and incubated within a PS plate. The attached cells were washed with pure water, and released cells were recovered. The recovered cells were suspended again in a KCl solution, and seeded on a PS plate again. The attaching and releasing were repeated in the same manner. The attaching and releasing operations were repeated three times, and the attached cells at each point (before the initial release, and after first, second and third releases) were visualized by crystal violet staining. In addition, the staining agent was eluted from the cells, and quantified by measuring the absorbance at 590 nm ($A_{590}$). The result is shown by the average±standard error obtained by the three independent experiments (n=3).

Using the above-described adhesive properties of AtaA and adhesive properties of microorganism imparted by AtaA, it was attempted to release the microbial cells, which had been once immobilized by AtaA, by washing with pure water. The ADP1(pAtaA) cells, which had been immobilized on a PS plate or glass plate in 100 mM KCl, was washed with pure water or 100 mM KCl. As a result, it was shown that the microbial cells were effectively removed from the both plates by washing with pure water (FIG. 4). Of course the microbial cells could not be removed by washing with 100 mM KCl. Furthermore, it was studied whether the microbial cells once released by washing with pure water can be immobilized again and whether the attaching and releasing can be repeated. Firstly, the ADP1(pAtaA) cells were immobilized on a PS plate, and then released by washing with pure water. The released cells were suspended again in a 100 mM KCl aqueous solution, and immobilized again on a PS plate. This operation was repeated, thereby repeating attaching and releasing ADP1(pAtaA) cells. As a result, there was no decrease in immobilization efficiency even for the cells after repeating three times of attaching and releasing, which proves that attaching and releasing are repeatable (FIG. 5). Whether AtaA was kept to be properly displayed on the surface of the cells released at the end of the repetition operation was checked by flow cytometry; it was confirmed that the amount of displayed AtaA molecules on the cell surface was totally unchanged from the time before the first release (the result not shown). These experimental results indicate that AtaA will not be destroyed by washing-release, and its adhesion function will not be impaired.

Figure 6:
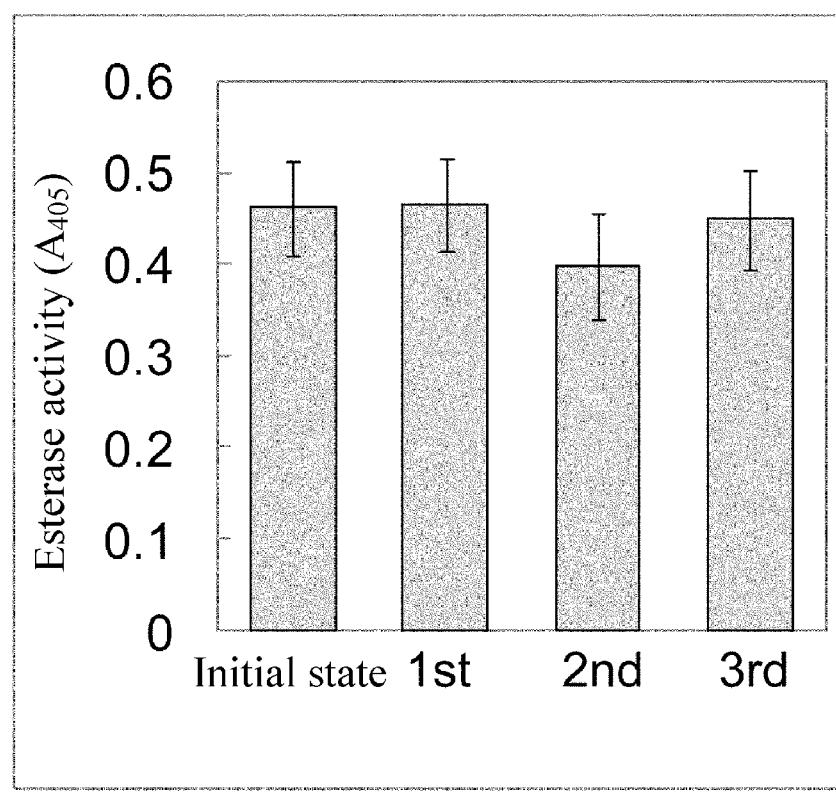
FIG. 6 shows the esterase activity of the immobilized ADP1(pAtaA) cells subjected to repeated attaching and releasing from a PS plate. Before the first release and in each time of attaching and releasing operation (first, second, and third), the ADP1(pAtaA) cells immobilized on a PS plate were washed with a KCl solution in the plate well. After washing, 200 μl of esterase reactant solution (1.9 mM paranitrophenylbutyric acid, 1.1% triton-X 100, 50 mM 3,3-dimethylglutaric acid, 50 mM tris, 50 mM 2-amino-2-methyl-1,3-propanediol) was added to the plate wells having immobilized cells, incubated for 30 minutes at room temperature, and then the absorbance at 405 nm was measured with a microplate reader, thereby detecting esterase activity. The result is shown by the average±standard error obtained by the three independent experiments (n=3).

Finally, with the aim of actually applying the technique of attaching and releasing the microorganism immobilized by AtaA, which has been developed this time, to bioprocess, the change in the enzymatic activity of the immobilized cells was studied by repeating the attaching and releasing. The ADP1 cells originally have esterase on the cell surface. Therefore, using the esterase activity as the index, the influence of attaching and releasing on the catalyst function of a whole cell catalyst was evaluated. The immobilized ADP1(pAtaA) cells were released with pure water, suspended again in a 100 mM KCl solution, and immobilized again, and then the immobilized microorganism cells were subjected to the quantification of the esterase activity. The attaching and releasing operation and esterase activity measurement were repeated. The result indicates that the esterase activity of the immobilized microorganism cells did not decrease even after repetition of the attaching and releasing (FIG. 6). More specifically, it is shown that the function of the whole cell catalyst will not decrease even after repetition of release and re-immobilizing of the microbial cells that have been immobilized by AtaA, so that the immobilizing cells are repeatedly usable.

As described above, the method for directly immobilizing a microorganism using AtaA is applicable to various microorganisms and carriers, and is a unique and versatile technique for immobilizing a whole cell catalyst without the problems of prior art immobilization methods. This novel method allows repeating attaching and releasing immobilized microbial cells with keeping their catalyst function, and contributes to the design of a more flexible and practical bioprocess.

B. Attaching and Releasing Experiment
(Immobilizing and Release of Bacterial Cells on Sponge)

Figure 7:
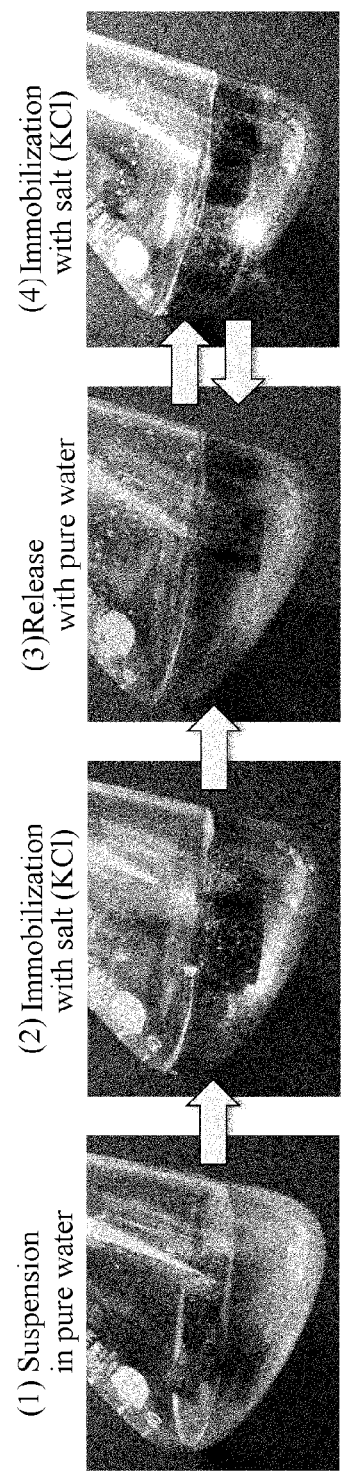
FIG. 7 shows the result of attaching and releasing experiment. (1) The bacterial cells were suspended in pure water, and a black sponge (polyurethane foam) was introduced therein. (2) A salt (KCl) solution was added and shaken (immobilization). (3) Pure water was added and shaken (releasing). (4) A salt (KCl) solution was added and shaken (immobilization).

The ADP1(pAtaA) cells were suspended in pure water in a conical flask, and then a black sponge (polyurethane foam) was put in. Firstly, the liquid was turbid because of the bacterial cells dispersed in the liquid (FIG. 7(1)). After adding a salt (KCl) solution, the liquid was shaken. Then, the bacterial cells adhered to the sponge, and the suspension turned transparent (FIG. 7(2)). The black sponge appeared to be whitish because of the bacterial cells adhered to the surface. When the salt solution was substituted with pure water and shaken, the bacterial cells immobilized on the sponge were released and suspended in pure water, so that the liquid turned cloudy (FIG. 7(3)). When a salt solution was added and shaken, the bacterial cells were immobilized again on the sponge and the liquid turned transparent (FIG. 7(4)). Shaking and addition of a salt solution/substitution with pure water and shaking are carried out alternately, the above-described attaching and releasing can be repeated.

INDUSTRIAL APPLICABILITY

The method of the present invention allows releasing and recovering a microorganism which has been immobilized (attached) on a carrier, immobilizing the recovered microorganism on the carrier again, and further repeating the immobilizing and releasing. The present invention realizing such use of a microorganism by simple operations will bring about innovative effect in the bioprocess using an immobilized microorganism. Of special note is that the immobilized microorganism can be released by an extremely simple operation. The use of the method of the present invention allows free reuse of a microorganism and a carrier, such as the use of a once used immobilized microorganism by immobilizing it again on another carrier, replacement of a microorganism having weakened activity on a carrier with a fresh cells having high activity, or re-activation and re-immobilization of released cells having decreased activity. The present invention is widely useful, and is useful for, for example, conventional fermentation industry and waste disposal, and is markedly effective for the production of biomass energy and green biotechnology using microbial cells. The application of the present invention will allow cost reduction, improvement of efficiency of the production process, and the like.

The present invention will not be limited to the description of the embodiments and examples of the present invention. Various modifications readily made by those skilled in the art are also included in the present invention, without departing from the scope of claims. The entire contents of the articles, unexamined patent publications, and patent applications specified herein are hereby incorporated herein by reference.

SEQUENCE LIST FREE TEXT

SEQ ID NO. 7: Explanation of artificial sequence: primer
SEQ ID NO. 8: Explanation of artificial sequence: primer
SEQ ID NO. 9: Explanation of artificial sequence: primer
SEQ ID NO. 10: Explanation of artificial sequence: primer
SEQ ID NO. 11: Explanation of artificial sequence: recognition sequence of HRV 3C protease

The invention claimed is:

1. A method for attaching and releasing a microorganism comprising the following steps (1) and (2):
   (1) contacting a microorganism, into which DNA encoding an autotransporter adhesion derived from the ataA gene of a microorganism belonging to the genus *Acinetobacter* has been introduced to impart or enhance non-specific adhesiveness, with a carrier under a high ionic strength and thus attaching the microorganism to the carrier; and
   (2) releasing the microorganism from the carrier by washing under a low ionic strength,
   wherein the high ionic strength is from 20 mM to 200 mM, and the low ionic strength is less than 10 mM.

2. The method of claim 1, wherein the *Acinetobacter* is *Acinetobacter* sp. Tol 5.

3. The method of claim 1, wherein the DNA is any of (a), (b) or (c):
   (a) DNA composed of the base sequence of SEQ ID NO: 1;
   (b) DNA composed of the base sequence having 90% or more homology with the base sequence of SEQ ID NO: 1, and encoding the protein having activity of imparting or enhancing non-specific adhesiveness to a microorganism;
   (c) DNA composed of a part of the base sequence of SEQ ID NO: 1, and encoding the protein having activity of imparting or enhancing non-specific adhesiveness to a microorganism.

4. The method of claim 3, wherein the DNA of the following (a) or (b) is introduced into the microorganism together with the DNA encoding an autotransporter adhesin:
   (a) DNA composed of the base sequence of SEQ ID NO: 3;
   (b) DNA composed of the base sequence having 90% or more homology with the base sequence of SEQ ID NO: 3.

5. The method of claim 1, wherein the DNA of the following (a) or (b) including the above-described DNA has been introduced into the microorganism:
   (a) DNA composed of the base sequence of SEQ ID NO: 5;
   (b) DNA composed of the base sequence having 90% or more homology with the base sequence of SEQ ID NO: 5, and having activity of imparting or enhancing non-specific adhesiveness to a microorganism.

6. The method of claim 1, wherein the following step (3-1) is carried out after the step (2):
   (3-1) recovering the released microorganism.

7. The method of claim 1, wherein the following step (3-2) is carried out after the step (2):
(3-2) recovering the carrier.

8. The method of claim 1, wherein the following step (i) is carried out between the steps (1) and (2):
(i) contacting the microorganism attached to the carrier with a liquid to be treated, and keeping the contact state.

9. The method of claim 8, wherein the microorganism produces a specific enzyme, and the liquid to be treated comprises a substrate of the specific enzyme that is treated by the specific enzyme.

10. The method of claim 1, wherein the microorganism is a microorganism belonging to the genus *Escherichia*.

\* \* \* \* \*

SEQUENCE LISTING

<160> NUMBER OF SEQ ID NOS: 12

<210> SEQ ID NO 1
<211> LENGTH: 10893
<212> TYPE: DNA
<213> ORGANISM: Acinetobacter sp

<400> SEQUENCE: 1

| | | | | | | |
|---|---|---|---|---|---|---|
| atgaataaaa | tctacaaagt | gatttggaat | gcgactttgt | tggcatgggt | tgcagtatct | 60 |
| gaattggcaa | aagggaaaac | caaatctacg | acatcaaaat | ccaaagctaa | atcattatct | 120 |
| tcatctgtaa | tagttggtgg | gataatatta | acaacacctt | tatctttaat | agcagctact | 180 |
| gttcaagttg | gaggggggaac | taattctgga | acaactgcta | cagcttctac | gaattgtgca | 240 |
| gacttatata | attatcaaaa | tcctgagaac | tcaggctctg | gagcggctgg | gaattataat | 300 |
| gcaggaaatc | caagtgtgtg | ttcgatcgct | ataggtgaaa | acgcacaagg | tggtacttct | 360 |
| ggaactggag | ggtcgccagg | gatagcgata | ggtggaaatt | ctaaagctac | gggtggttta | 420 |
| tctgttgcta | taggcggata | tgctcaagcg | acaaatgttg | gaagtattgc | tttaggcaca | 480 |
| gcagctttat | caagtggttt | taacagttta | gcaatatcca | gacaagctgc | tgcaacgaat | 540 |
| aactattcaa | tagctatagg | tacaacttca | gtttcgaaag | gagttggatc | gattgctatg | 600 |
| gggcattcaa | cgaatgcttc | tggagatcaa | tcgatagcaa | ttggtagctc | ggatgctgtt | 660 |
| aattcagcaa | cagcaacaac | aacatacgat | ggtacaacaa | atactcaagc | atcaggtagt | 720 |
| aaatcgattg | ctataggtgc | aagcgcaaag | gcatcaacca | ataacagcat | tgcactaggt | 780 |
| gcaggatcgg | taacttctgc | acaatctggt | aattcttatc | ttactggtgt | aggtgcatca | 840 |
| gctacaaatg | tgttgtatc | tgttggaact | tcaactgcaa | cacgtcgtat | ccaaaatgta | 900 |
| gcagatggtt | cagccgcttc | agatgctgtg | acagttgctc | agttggataa | agcttatgat | 960 |
| gatacaaatg | tcgtttagc | tgctgcttta | ggtacaggta | gtggtgctgc | ctataatgca | 1020 |
| gcaaacaata | catataccgc | tccaacgaat | attggggggaa | caggtaaaaa | tacgattgat | 1080 |
| gatgcaatta | aagcaactca | acgaagtgta | gtcgctggat | caaatattgt | cgttaccccg | 1140 |
| acgacagctt | ctgatggttc | aatatcgtat | tcggttgcta | caagcgcaac | accgacgttt | 1200 |
| acaagtataa | ctgtaaacaa | tgcaccaacg | gcaggtacag | atgcgaccaa | caagacttat | 1260 |
| gtagactcaa | aagcagcagc | atcgagaaca | gaagtagcag | ctggaagcaa | tgtatctggt | 1320 |
| gtagtaaaaa | cgacaggcgc | aaacggtcaa | gacgtttata | cagtaaatgc | caatggtacg | 1380 |
| actgcatcag | caggttcttc | agcagttacc | gtaacaccag | gcacgaaaga | tgcaaataat | 1440 |
| gtcactgact | ataaagtaga | cttatcagcg | actacaaaaa | ccgatatcca | aaaaggtgta | 1500 |
| gatgcaaaaa | atgctgtaga | taccgcaggt | ctaaaattta | aaggtgatac | agcaaccaca | 1560 |
| agcaatacca | agaaattagg | tgacaccgtt | tcgattacgg | gtgatacgaa | cattagtaca | 1620 |
| gttgcgacaa | cagatggtgt | acaggttaag | ttaaatccaa | acttggattt | aggagcaact | 1680 |
| ggtagcgtta | aaacgggtaa | taccacgatt | aacaatgcag | gtgtaacagc | tgatcaagtt | 1740 |
| acggttggtg | gtgttgttat | taacaacaca | tcaggtatta | tgctggtgg | taaagcgatt | 1800 |
| actaatgtag | cagcaccaac | aaataacaca | gatgctgcta | caagaagta | tgtagatgat | 1860 |
| gcaggtacag | cattaaccaa | tttgggcttt | ggattaaaag | cacaagatgg | tacgactgtg | 1920 |
| aacaagaaat | taggtgaagc | agttgatatt | gttggttcaa | acagcaacat | cagtacaaaa | 1980 |
| gtaaatgcag | gcaaagtaga | agttgcacta | tccaatacat | tggacttagg | tactacaggt | 2040 |
| agcgttacta | cgggttcaac | tgtaattaac | aatgctggtg | ttacggcaac | tcaagttacc | 2100 |

```
gcaaacaaag tcacaataaa caatgcacca acagcaggta cagatgcgac caacaagact    2160
tatgtagact caaaagcagc agcatcaaga acagaagtcg cagctggaag caatgtatct    2220
ggtgtagtaa aaacgacagg cgcaaacggt caagatattt atgcagtaaa tgccaatggt    2280
acgactgcat cagcaggttc ttcagcagtt accgtaacac caggcacgaa agatgcaaat    2340
aatgtcactg actataaagt agacttgtca gcgactacaa aaccgatat tcaaaaggt     2400 gtagatgcaa aaaatgctgt agatactgca ggtctaaaat ttaaaggtga tacagcaacc    2460
acaagcaata ccaagaaatt aggtgacacc gtttcgatta cgggtgatac gaacattagt    2520
acagttgcaa caactgatgg tgtacaggtt aagttaaatc caaacttaga tttaggagca    2580
actggtagcg ttaaaacggg taataccacg attaacaatg caggtgtaac agctgaccaa    2640
gttacggttg gtggtgttgt tattaacaac acatcaggta ttaatgctgg tggtaaagcg    2700
attaccaatg tagcagcacc aacaaataac acagatgctg ctaacaagaa gtatgtagat    2760
gacgcaggta cagcattaac caatttgggc tttggattaa aagcgcaaga tggtacgact    2820
gtgaacaaga aattaggtga agcagttgat attgttggtt caaacagcaa catcagtaca    2880
aaagtaaatg caggcaaagt agaagttgca ctatccaata cattggactt aggtactaca    2940
ggtagcgtta ctacgggttc aactgtaatt aacaatgctg gtgttacggc aactcaagtt    3000
accgcaaaca aagtcacagt taataatgca ccaacagcag gtacagatgc gaccaataaa    3060
acttatgtag actcaaaagc agcggcatca agaacagaag tcgcagctgg aagcaatgta    3120
tctggcgtag taaaaacgac aggtgcaaac ggtcaagacg tttatacagt aaatgccaat    3180
ggtacgactg catcagcagg ttcttcagca gttaccgtaa caccaggcac gaaagatgca    3240
aataatgtca ctgactataa agtagacttg tcagcgacta caaaaaccga tattcaaaaa    3300
ggtgtagatg caaaaaatgc tgtagatacc gcaggtctaa aatttaaagg tgatacagca    3360
accacaagca ataccaagaa attaggtgac accgtttcga ttacgggtga tacgaacatt    3420
agtacagttg cgacaactga tggtgtacag gttaagctaa atccaaactt ggatttagga    3480
gcaactggta gcgttaaaac gggtaatacc acgattaaca atgcaggtgt aacagctgat    3540
caagttacag ttggtggtgt tgttattaac aacacatcag gtattaatgc tggtggtaaa    3600
gcgattacca atgtagcagc accaacaaat aacacagatg ctgctaacaa gaagtatgta    3660
gatgatgcag gtacagcatt aaccaatttg gcctttggat aaaagcgca agatggtacg    3720 actgtgaaca agaaattagg cgaagcagtt gaagttgttg gtgcggacag taacatcacc    3780
acgaaagttg caggcggtca ggttgcaatt gagttaaata aaaaccctcaa caacttaact    3840 ggcattaccg tgaacgatgg aaccaatggc accaatggtt caactgtgat tggtaaagat    3900
ggtatttcgg ttaaagatgg ttcaggcaat accattgcag gtgtagataa cacagcgttg    3960
acagttaaag atggcagtgg caacacagaa accagcatta accaagcgat caacacgtta    4020
aatgcagcgc aaggtgaaac tgataagttt gcagtgaagt acgacaaaaa tgctgatggc    4080
agtgtgaact acaacaacat cacattggca ggtacgactg caagcagtac acaagatgca    4140
actacaggca agatcaccac aacaggtgga acaagcttga acaatgttgc aagtgcgggt    4200
gactacaaag atgttgccaa tgcaagcaaa ggtgtaaacg caggtgactt aaacaatgca    4260
gttgttgatg caaccaatgc agcaaccagc aaaggctttg cattacaagc agcagatggc    4320
gctaaagttc agaagaacct aggcgaagca gttgaagttg tcggtgccga cagcaacatc    4380
accacaaaag ttgcaggcgg tcaggttgca attgagttaa ataaaaaccct caacaactta    4440
```

```
actggcatta ccgtgaacga tggaaccaat ggcaccaatg gttcaactgt gattggtaaa      4500
gatggtattt cagttaaaga cggttcaggc aataccattg caggtgtaga taacacagcg      4560
ttgacagtta agatggcag tggcaacaca gaaaccagca ttaaccaagc gatcaacacg       4620
ttaaatgcag cgcaaggtga aactgataag tttgcagtga agtacgacaa aaatacggat      4680
ggtagtacca actacaacag tattactgca ggcaatggta acggtactgc agcaacgatc      4740
ggaactgaca cagcaggtaa tagtgttgtg accagtggcg gaactaaaat tagtaatgtt      4800
gcgaatggtg tcaatgcaag tgatgcagta acaaaggtc aattggatag cttaagtaca       4860
ggtcttacca atacaggctt tggtttaaaa gcagcagatg gcaacaccgt taacaaaaaa      4920
ttaggcgaag cagtagacgt tgtcggtgct gacagcaaca tcaccacgaa agttgcaggc      4980
ggtcaggttg cgattgagtt aaataaaaac ctcaacaact taactggcat taccgtgaac      5040
gatggaacca atggcaccaa tggttcaact gtgattggta agatggtat ttcgattaaa       5100 gatggttcag gcaataccat tgcaggtgta gataacacag cgttgacagt taaagatggc      5160
agtggcaaca cagaaaccag cattaaccaa gcgatcaaca cgttaaatgc agcgcaaggt      5220
gaaactgaca gtttgcagt gaagtacgac aagaatgctg atggcagtgc aaactacaac       5280
aacatcacat ggcaggtac gactgcaagt agcacgcaag atgcaacaac aggcaagatc       5340
accacaacag gtggaacaag cttgaacaac gttgcaagtg caggtgacta caagatgtt       5400 gccaatgcaa gcaaaggtgt aaacgcaggt gacttgaaca atgcagttgt tgatgcaacc      5460
aatgcagcaa ccagcaaagg ctttgcatta caagcagcag atggcgctaa agttcagaag      5520
aacctaggcg aagcagttga agttgtcggt gcggacagca acatcaccac aaaagtagtg      5580
ggtggacaag ttgcgattga gttaaataaa aacctcaaca acttaactgg cattaccgtg      5640 aacgatgaa ccaatggcac aaatggttca actgtgattg gtaaagatgg tatttcggtt       5700
aaagatggtt caggtaatac cattgcaggt gtagataaca cagcgttgac agttaaagat      5760
ggcagtggca acacagaaac cagcattaac caagcgatca cacgttaaa tgcagcgcaa       5820 ggtgaaactg ataagtttgc agtgaagtac gacaaaaatg ctgatggcag tgtgaactac      5880
aacaacatca cattggcagg tacgactgca agcagtacac aagatgcaac tacaggcaag      5940
atcaccacaa caggtggaac aagcttgaac aatgttgcaa gtgcgggtga ctacaaagat      6000
gttgccaatg caagcaaagg tgtaaacgca ggtgacttaa acaatgcagt tgttgatgca      6060
accaatgcag caaccagcaa aggctttgca ttacaagcag cagatggcgc taaagttcag      6120
aagaacctag gcgaagcagt tgaagttgtc ggtgccgaca gcaacatcac cacaaaagtt      6180
gcaggcggtc aggttgcaat tgagttaaat aaaaacctca caacttaac tggcattacc       6240 gtgaacgatg gaaccaatgg caccaatggt tcaactgtga ttggtaaaga tggtatttca      6300
gttaaagacg gttcaggcaa taccattgca ggtgtagata acacagcgtt gacagttaaa      6360
gatggcagtg gcaacacaga accagcatt aaccaagcga tcaacacgtt aaatgcagcg      6420
caaggtgaaa ctgataagtt tgcagtgaag tacgacaaaa atgctgatgg cagtgtgaac      6480
tacaacaaca tcacattggc aggtacgact gcaagcagta cacaagatgc aactacaggc      6540
aagatcacca caacaggtgg tacaagcttg aacaatgttg caagtgcggg tgactacaaa      6600
gatgttgcca atgcaagcaa aggtgtaaac gcaggtgact tgaacaatgc agttgttgat      6660
gcaaccaatg cagcgaccag caaaggcttt gcattacaag cagcagatgg cgctaaagtt      6720
cagaagaacc taggcgaagc agttgaagtt gttggtgcgg acagtaacat caccacgaaa      6780
gttgcaggcg gtcaggttgc aattgagtta aataaaaacc tcaacaactt aactggcatt      6840
```

```
accgtgaacg atggaaccaa tggcaccaat ggttcaactg tgattggtaa agatggtatt    6900
tcggttaaag atggttcagg caataccatt gcaggtgtag ataacacagc gttgacagtt    6960
aaagatggca gtggcaacac agaaaccagc attaaccaag cgatcaacac gttaaatgca    7020
gcgcaaggtg aaactgataa gtttgcagtg aagtacgaca aaaatgctga tggcagtgca    7080
aactataaca atgtcacttt agctggtaca aatggcacaa taatcagcaa tgttaaagcg    7140
ggtgctgtga cctcaacatc tactgatgcg atcaatggta gccaattata tggtgttgca    7200
aacagcgtga agaatgcaat tggtggttca accacaattg atgcaacgac tggtgcaatc    7260
acgacgacca atattggtgg tacaggttca aatacgattg atggtgcaat cagcagtatt    7320
aaagattcag cgactaaagc gaaaaccacg gtaagtgctg gggataatgt tgtcgttaca    7380
tcgggtacca atgcagatgg ctcaacaaac tatgaagttg cgacagcgaa agacgttaac    7440
tttgacaaag tgactgtagg tagtgttgtt gtagataaat caagcaatac aatcaaagga    7500
ttaagtaata ccacttggaa cggaacagca gtatcaggtc aagcggcgac agaagaccag    7560
ttaaaaacgg tcagcgatgc gcaaggtgaa actgataagt ttgcagtgaa gtacgacaaa    7620
aatgctgatg gcagtgcgaa ctacaacagt attactgcag gcaatggtaa cggtactgca    7680
gcaacgatcg gaactgacac agcaggtaat agtgttgtga ccagtggcgg aactaaaatt    7740
agtaatgttg cgaatggtgt caatgcaagt gatgcagtaa acaaaggtca attggatagc    7800
ttaagtacag gtcttaccaa tacaggcttt ggtttaaaag cagcagatgg caacaccgtt    7860
aacaaaaaat taggcgaagc agtagacgtt gtcggtgctg acagcaacat caccacgaaa    7920
gttgcaggcg gtcaggttgc gattgagtta aataaaaacc tcaacaactt aactggcatt    7980
accgtgaacg atggaaccaa tggcaccaat ggttcaactg tgattggtaa agatggtatt    8040
tcgattaaag atggttcagg caataccatt gcaggtgtag ataacacagc gttgacggtt    8100
aaagatagca gtggcaacac agaaaccagc attaaccaag cgatcaacac gttaaatgca    8160
gcgcaaggtg aaactgataa gtttgcagtg aagtacgata agaatgctga tggcagtgtg    8220
aactataaca atgtcacttt agcaggtaca aatggcacaa taatcagaaa tgttaaagcg    8280
ggtgctgtga cctcaacatc tactgatgcg atcaatggta gccaattata cgatattgca    8340
aacagcgtga agaatgcaat tggtggttca accacaagag atgtaacgac tggtgcaatc    8400
acaacgacca atattggtgg tacaggttca aacacgattg atggtgcaat cagcagtatt    8460
aaagattcag cgactaaagc gaaaaccacg ataagtgctg gggataatgt tgtcgttaca    8520
tcgggtacca atgcagatgg ctcaacaaac tatgaagttg cgacagcgaa agacgttaac    8580
tttgacaaag taactgtagg taatgttgtt gttgataagg caaatgacac gatccaaggt    8640
ttgagcaata aagatctaaa ttcaactgat tttgcgacca aggtagagc tgcgactgaa    8700 gaacagttaa aagcagtgat taccagtaat atcacggaag ttgtggatgg taatggcaac    8760
aaggtgaata ttattgacca agttgtaaat accaaacctg acaataagaa ccaagattca    8820
ttgttcttaa cgtatgacaa acaaggtcaa gaaaccacag atcgcctaac gattggtcaa    8880
acggtacaga agatgaatac tgatggtatt aaattcttcc ataccaatgc cgatacatca    8940
aaaggtgatt tgggtacaac aaaatgactca agtgcaggtg gtttaaactc tacagcaatt    9000
ggtgtaaatg cgattgttgc gaatggtgca gatagttcag ttgctttagg tcataacacc    9060
aaagtcaatg gtaaacaatc aattgcaatt ggttctggtg cagaagcttt aggcaatcaa    9120
tcgatcagta ttggtacagg caataaagtc actggtgatc attcgggtgc gattggtgat    9180
```

-continued

```
ccaactattg taaatggtgc aaacagctac tctgtgggta ataacaacca agtacttaca    9240
gatgacactt tcgtacttgg aaacaatgtc accaaaacta ttgctggttc agtagtattg    9300
ggtaacggtt cagctgcaac gacaggtgct ggtgaggcag gctatgcctt atctgtagca    9360
acaaatgcag ataaagccgc gatcactaaa actacgtcaa gcactggtgc tgttgcagtt    9420
ggtgatgcgt cgagcggtat ttatcgtcaa attaccggtg ttgctgcggg tagcgtagat    9480
tcagatgctg tgaacgttgc acagttaaaa gcggtgggta accaagttgt aacgactcaa    9540
actacattgg tgaacagttt gggtggtaac gctaaagtaa atgcagacgg tacgattaca    9600
ggaccaactt ataatgttgc tcaaggtaat cagaccaatg ttggtgatgc attaactgcg    9660
cttgataacg caattaatac tgcggcaaca acatctaaat cgactgtttc taatggtcag    9720
aatattgttg tcagcaagag caaaaatgca gatggttcag acaactatga agtatcaaca    9780
gcaaaagact tgacagttga ttctgtcaaa gcgggtgata cggttctgaa taatgcaggt    9840
attacaattg gcaataacgc agttgtattg aacaacactg gattaaccat tagtggtgga    9900
ccaagtgtta ccttggcagg catcgatgca ggcaataaaa ccattcaaaa tgttgcgaat    9960
gcagtaaatg caacagatgc agtcaacaaa gggcaattgg acagcgcaat taacaatgtg   10020
aataacaatg taaatgagct tgccaacaac gctgttaaat atgacgatgc atcaaaagat   10080
aagatcacac ttggtggtgg ggcaactggt acaacaatca ccaatgtgaa agatggtact   10140
gttgcgcaag ttctaaaga tgctgtgaat ggcggtcaat tgtggaatgt tcaacaacaa    10200
gttgatcaga acacaactga tattagcaat atcaaaaatg atattaacaa cggtactgtt   10260
ggtttggttc aacaagcagg taaagatgca ccagtgacgg ttgcaaaaga tactggcggt   10320
acaacggtga atgtcgctgg aacagatggc aaccgagtag tgacaggtgt taaggaaggt   10380
gcagtgaatg caacatctaa agatgctgtc aatggtagtc aattgaatac aaccaaccaa   10440
gcggtagtca attatcttgg tggtggggca ggttatgaca acattacagg tagcttcaca   10500
gcgccaagtt atacggtagg tgactcgaaa tacaacaatg ttggtggcgc aattgatgca   10560
ttgaatcaag cagatcaagc attgaatagc aaaattgaca atgtcagtaa caagttggat   10620
aacgcattcc gtattaccaa caaccgtatt gatgatgtag agaaaaaagc caatgctggt   10680
attgccgctg cgatggctct ggaatcagca ccatatgtcc caggtaaata tacctatgca   10740
gcaggcgcag cttaccacgg tggtgaaaat gcggtaggtg tgactttacg taaaactgca   10800
gacaatggtc gttggtcgat tacaggcggt gtagctgcag cgtctcaagg cgatgcaagt   10860
gttcgtatcg gtatcagcgg tgtgattgac taa                                10893
```

<210> SEQ ID NO 2
<211> LENGTH: 3630
<212> TYPE: PRT
<213> ORGANISM: Acinetobacter sp

<400> SEQUENCE: 2

```
Met Asn Lys Ile Tyr Lys Val Ile Trp Asn Ala Thr Leu Leu Ala Trp
1               5                   10                  15

Val Ala Val Ser Glu Leu Ala Lys Gly Lys Thr Lys Ser Thr Thr Ser
                20                  25                  30

Lys Ser Lys Ala Lys Ser Leu Ser Ser Val Ile Gly Gly Ile
            35                  40                  45

Ile Leu Thr Thr Pro Leu Ser Leu Ile Ala Ala Thr Val Gln Val Gly
        50                  55                  60

Gly Gly Thr Asn Ser Gly Thr Thr Ala Thr Ala Ser Thr Asn Cys Ala
```

```
                65                  70                  75                  80
Asp Leu Tyr Asn Tyr Gln Asn Pro Glu Asn Ser Gly Ser Gly Ala Ala
                    85                  90                  95
Gly Asn Tyr Asn Ala Gly Asn Pro Ser Val Cys Ser Ile Ala Ile Gly
                100                 105                 110
Glu Asn Ala Gln Gly Gly Thr Ser Gly Thr Gly Gly Ser Pro Gly Ile
                115                 120                 125
Ala Ile Gly Gly Asn Ser Lys Ala Thr Gly Gly Leu Ser Val Ala Ile
130                 135                 140
Gly Gly Tyr Ala Gln Ala Thr Asn Val Gly Ser Ile Ala Leu Gly Thr
145                 150                 155                 160
Ala Ala Leu Ser Ser Gly Phe Asn Ser Leu Ala Ile Ser Arg Gln Ala
                165                 170                 175
Ala Ala Thr Asn Asn Tyr Ser Ile Ala Ile Gly Thr Thr Ser Val Ser
                180                 185                 190
Lys Gly Val Gly Ser Ile Ala Met Gly His Ser Thr Asn Ala Ser Gly
                195                 200                 205
Asp Gln Ser Ile Ala Ile Gly Ser Ser Asp Ala Val Asn Ser Ala Thr
210                 215                 220
Ala Thr Thr Thr Tyr Asp Gly Thr Thr Asn Thr Gln Ala Ser Gly Ser
225                 230                 235                 240
Lys Ser Ile Ala Ile Gly Ala Ser Ala Lys Ala Ser Thr Asn Asn Ser
                245                 250                 255
Ile Ala Leu Gly Ala Gly Ser Val Thr Ser Ala Gln Ser Gly Asn Ser
                260                 265                 270
Tyr Leu Thr Gly Val Gly Ala Ser Ala Thr Asn Gly Val Val Ser Val
                275                 280                 285
Gly Thr Ser Thr Ala Thr Arg Arg Ile Gln Asn Val Ala Asp Gly Ser
290                 295                 300
Ala Ala Ser Asp Ala Val Thr Val Ala Gln Leu Asp Lys Ala Tyr Asp
305                 310                 315                 320
Asp Thr Asn Gly Arg Leu Ala Ala Ala Leu Gly Thr Gly Ser Gly Ala
                325                 330                 335
Ala Tyr Asn Ala Ala Asn Asn Thr Tyr Thr Ala Pro Thr Asn Ile Gly
                340                 345                 350
Gly Thr Gly Lys Asn Thr Ile Asp Asp Ala Ile Lys Ala Thr Gln Arg
                355                 360                 365
Ser Val Val Ala Gly Ser Asn Ile Val Val Thr Pro Thr Thr Ala Ser
                370                 375                 380
Asp Gly Ser Ile Ser Tyr Ser Val Ala Thr Ser Ala Thr Pro Thr Phe
385                 390                 395                 400
Thr Ser Ile Thr Val Asn Asn Ala Pro Thr Ala Gly Thr Asp Ala Thr
                405                 410                 415
Asn Lys Thr Tyr Val Asp Ser Lys Ala Ala Ser Arg Thr Glu Val
                420                 425                 430
Ala Ala Gly Ser Asn Val Ser Gly Val Val Lys Thr Gly Ala Asn
                435                 440                 445
Gly Gln Asp Val Tyr Thr Val Asn Ala Asn Gly Thr Thr Ala Ser Ala
                450                 455                 460
Gly Ser Ser Ala Val Thr Val Thr Pro Gly Thr Lys Asp Ala Asn Asn
465                 470                 475                 480
Val Thr Asp Tyr Lys Val Asp Leu Ser Ala Thr Thr Lys Thr Asp Ile
                485                 490                 495
```

-continued

```
Gln Lys Gly Val Asp Ala Lys Asn Ala Val Asp Thr Ala Gly Leu Lys
        500                 505                 510
Phe Lys Gly Asp Thr Ala Thr Thr Ser Asn Thr Lys Lys Leu Gly Asp
        515                 520                 525
Thr Val Ser Ile Thr Gly Asp Thr Asn Ile Ser Thr Val Ala Thr Thr
        530                 535                 540
Asp Gly Val Gln Val Lys Leu Asn Pro Asn Leu Asp Leu Gly Ala Thr
545                 550                 555                 560
Gly Ser Val Lys Thr Gly Asn Thr Thr Ile Asn Asn Ala Gly Val Thr
                565                 570                 575
Ala Asp Gln Val Thr Val Gly Val Val Ile Asn Asn Thr Ser Gly
        580                 585                 590
Ile Asn Ala Gly Gly Lys Ala Ile Thr Asn Val Ala Ala Pro Thr Asn
        595                 600                 605
Asn Thr Asp Ala Ala Asn Lys Lys Tyr Val Asp Ala Gly Thr Ala
        610                 615                 620
Leu Thr Asn Leu Gly Phe Gly Leu Lys Ala Gln Asp Gly Thr Thr Val
625                 630                 635                 640
Asn Lys Lys Leu Gly Glu Ala Val Asp Ile Val Gly Ser Asn Ser Asn
                645                 650                 655
Ile Ser Thr Lys Val Asn Ala Gly Lys Val Glu Val Ala Leu Ser Asn
                660                 665                 670
Thr Leu Asp Leu Gly Thr Thr Gly Ser Val Thr Thr Gly Ser Thr Val
        675                 680                 685
Ile Asn Asn Ala Gly Val Thr Ala Thr Gln Val Thr Ala Asn Lys Val
        690                 695                 700
Thr Ile Asn Asn Ala Pro Thr Ala Gly Thr Asp Ala Thr Asn Lys Thr
705                 710                 715                 720
Tyr Val Asp Ser Lys Ala Ala Ser Arg Thr Glu Val Ala Ala Gly
                725                 730                 735
Ser Asn Val Ser Gly Val Val Lys Thr Thr Gly Ala Asn Gly Gln Asp
                740                 745                 750
Ile Tyr Ala Val Asn Ala Asn Gly Thr Thr Ala Ser Ala Gly Ser Ser
        755                 760                 765
Ala Val Thr Val Thr Pro Gly Thr Lys Asp Ala Asn Asn Val Thr Asp
        770                 775                 780
Tyr Lys Val Asp Leu Ser Ala Thr Thr Lys Thr Asp Ile Gln Lys Gly
785                 790                 795                 800
Val Asp Ala Lys Asn Ala Val Asp Thr Ala Gly Leu Lys Phe Lys Gly
                805                 810                 815
Asp Thr Ala Thr Thr Ser Asn Thr Lys Lys Leu Gly Asp Thr Val Ser
                820                 825                 830
Ile Thr Gly Asp Thr Asn Ile Ser Thr Val Ala Thr Asp Gly Val
        835                 840                 845
Gln Val Lys Leu Asn Pro Asn Leu Asp Leu Gly Ala Thr Gly Ser Val
        850                 855                 860
Lys Thr Gly Asn Thr Thr Ile Asn Asn Ala Gly Val Thr Ala Asp Gln
865                 870                 875                 880
Val Thr Val Gly Gly Val Val Ile Asn Asn Thr Ser Gly Ile Asn Ala
                885                 890                 895
Gly Gly Lys Ala Ile Thr Asn Val Ala Ala Pro Thr Asn Asn Thr Asp
        900                 905                 910
```

```
Ala Ala Asn Lys Lys Tyr Val Asp Asp Ala Gly Thr Ala Leu Thr Asn
            915                 920                 925

Leu Gly Phe Gly Leu Lys Ala Gln Asp Gly Thr Thr Val Asn Lys Lys
        930                 935                 940

Leu Gly Glu Ala Val Asp Ile Val Gly Ser Asn Ser Asn Ile Ser Thr
945                 950                 955                 960

Lys Val Asn Ala Gly Lys Val Glu Val Ala Leu Ser Asn Thr Leu Asp
                965                 970                 975

Leu Gly Thr Thr Gly Ser Val Thr Thr Gly Ser Thr Val Ile Asn Asn
            980                 985                 990

Ala Gly Val Thr Ala Thr Gln Val Thr Ala Asn Lys Val Thr Val Asn
            995                 1000                1005

Asn Ala Pro Thr Ala Gly Thr Asp Ala Thr Asn Lys Thr Tyr Val
        1010                1015                1020

Asp Ser Lys Ala Ala Ala Ser Arg Thr Glu Val Ala Ala Gly Ser
        1025                1030                1035

Asn Val Ser Gly Val Val Lys Thr Thr Gly Ala Asn Gly Gln Asp
        1040                1045                1050

Val Tyr Thr Val Asn Ala Asn Gly Thr Thr Ala Ser Ala Gly Ser
        1055                1060                1065

Ser Ala Val Thr Val Thr Pro Gly Thr Lys Asp Ala Asn Asn Val
        1070                1075                1080

Thr Asp Tyr Lys Val Asp Leu Ser Ala Thr Thr Lys Thr Asp Ile
        1085                1090                1095

Gln Lys Gly Val Asp Ala Lys Asn Ala Val Asp Thr Ala Gly Leu
        1100                1105                1110

Lys Phe Lys Gly Asp Thr Ala Thr Thr Ser Asn Thr Lys Lys Leu
        1115                1120                1125

Gly Asp Thr Val Ser Ile Thr Gly Asp Thr Asn Ile Ser Thr Val
        1130                1135                1140

Ala Thr Thr Asp Gly Val Gln Val Lys Leu Asn Pro Asn Leu Asp
        1145                1150                1155

Leu Gly Ala Thr Gly Ser Val Lys Thr Gly Asn Thr Thr Ile Asn
        1160                1165                1170

Asn Ala Gly Val Thr Ala Asp Gln Val Thr Val Gly Gly Val Val
        1175                1180                1185

Ile Asn Asn Thr Ser Gly Ile Asn Ala Gly Gly Lys Ala Ile Thr
        1190                1195                1200

Asn Val Ala Ala Pro Thr Asn Asn Thr Asp Ala Ala Asn Lys Lys
        1205                1210                1215

Tyr Val Asp Asp Ala Gly Thr Ala Leu Thr Asn Leu Gly Phe Gly
        1220                1225                1230

Leu Lys Ala Gln Asp Gly Thr Thr Val Asn Lys Lys Leu Gly Glu
        1235                1240                1245

Ala Val Glu Val Val Gly Ala Asp Ser Asn Ile Thr Thr Lys Val
        1250                1255                1260

Ala Gly Gly Gln Val Ala Ile Glu Leu Asn Lys Asn Leu Asn Asn
        1265                1270                1275

Leu Thr Gly Ile Thr Val Asn Asp Gly Thr Asn Gly Thr Asn Gly
        1280                1285                1290

Ser Thr Val Ile Gly Lys Asp Gly Ile Ser Val Lys Asp Gly Ser
        1295                1300                1305

Gly Asn Thr Ile Ala Gly Val Asp Asn Thr Ala Leu Thr Val Lys
```

-continued

```
            1310                1315                1320
Asp Gly Ser Gly Asn Thr Glu Thr Ser Ile Asn Gln Ala Ile Asn
            1325                1330                1335
Thr Leu Asn Ala Ala Gln Gly Glu Thr Asp Lys Phe Ala Val Lys
            1340                1345                1350
Tyr Asp Lys Asn Ala Asp Gly Ser Val Asn Tyr Asn Asn Ile Thr
            1355                1360                1365
Leu Ala Gly Thr Thr Ala Ser Ser Thr Gln Asp Ala Thr Thr Gly
            1370                1375                1380
Lys Ile Thr Thr Thr Gly Gly Thr Ser Leu Asn Asn Val Ala Ser
            1385                1390                1395
Ala Gly Asp Tyr Lys Asp Val Ala Asn Ala Ser Lys Gly Val Asn
            1400                1405                1410
Ala Gly Asp Leu Asn Asn Ala Val Val Asp Ala Thr Asn Ala Ala
            1415                1420                1425
Thr Ser Lys Gly Phe Ala Leu Gln Ala Ala Asp Gly Ala Lys Val
            1430                1435                1440
Gln Lys Asn Leu Gly Glu Ala Val Glu Val Val Gly Ala Asp Ser
            1445                1450                1455
Asn Ile Thr Thr Lys Val Ala Gly Gly Gln Val Ala Ile Glu Leu
            1460                1465                1470
Asn Lys Asn Leu Asn Asn Leu Thr Gly Ile Thr Val Asn Asp Gly
            1475                1480                1485
Thr Asn Gly Thr Asn Gly Ser Thr Val Ile Gly Lys Asp Gly Ile
            1490                1495                1500
Ser Val Lys Asp Gly Ser Gly Asn Thr Ile Ala Gly Val Asp Asn
            1505                1510                1515
Thr Ala Leu Thr Val Lys Asp Gly Ser Gly Asn Thr Glu Thr Ser
            1520                1525                1530
Ile Asn Gln Ala Ile Asn Thr Leu Asn Ala Ala Gln Gly Glu Thr
            1535                1540                1545
Asp Lys Phe Ala Val Lys Tyr Asp Lys Asn Thr Asp Gly Ser Thr
            1550                1555                1560
Asn Tyr Asn Ser Ile Thr Ala Gly Asn Gly Asn Gly Thr Ala Ala
            1565                1570                1575
Thr Ile Gly Thr Asp Thr Ala Gly Asn Ser Val Val Thr Ser Gly
            1580                1585                1590
Gly Thr Lys Ile Ser Asn Val Ala Asn Gly Val Asn Ala Ser Asp
            1595                1600                1605
Ala Val Asn Lys Gly Gln Leu Asp Ser Leu Ser Thr Gly Leu Thr
            1610                1615                1620
Asn Thr Gly Phe Gly Leu Lys Ala Ala Asp Gly Asn Thr Val Asn
            1625                1630                1635
Lys Lys Leu Gly Glu Ala Val Asp Val Val Gly Ala Asp Ser Asn
            1640                1645                1650
Ile Thr Thr Lys Val Ala Gly Gly Gln Val Ala Ile Glu Leu Asn
            1655                1660                1665
Lys Asn Leu Asn Asn Leu Thr Gly Ile Thr Val Asn Asp Gly Thr
            1670                1675                1680
Asn Gly Thr Asn Gly Ser Thr Val Ile Gly Lys Asp Gly Ile Ser
            1685                1690                1695
Ile Lys Asp Gly Ser Gly Asn Thr Ile Ala Gly Val Asp Asn Thr
            1700                1705                1710
```

-continued

```
Ala Leu Thr Val Lys Asp Gly Ser Gly Asn Thr Glu Thr Ser Ile
1715                1720                1725

Asn Gln Ala Ile Asn Thr Leu Asn Ala Ala Gln Gly Glu Thr Asp
1730                1735                1740

Lys Phe Ala Val Lys Tyr Asp Lys Asn Ala Asp Gly Ser Ala Asn
1745                1750                1755

Tyr Asn Asn Ile Thr Leu Ala Gly Thr Thr Ala Ser Ser Thr Gln
1760                1765                1770

Asp Ala Thr Thr Gly Lys Ile Thr Thr Thr Gly Gly Thr Ser Leu
1775                1780                1785

Asn Asn Val Ala Ser Ala Gly Asp Tyr Lys Asp Val Ala Asn Ala
1790                1795                1800

Ser Lys Gly Val Asn Ala Gly Asp Leu Asn Asn Ala Val Val Asp
1805                1810                1815

Ala Thr Asn Ala Ala Thr Ser Lys Gly Phe Ala Leu Gln Ala Ala
1820                1825                1830

Asp Gly Ala Lys Val Gln Lys Asn Leu Gly Glu Ala Val Glu Val
1835                1840                1845

Val Gly Ala Asp Ser Asn Ile Thr Thr Lys Val Val Gly Gly Gln
1850                1855                1860

Val Ala Ile Glu Leu Asn Lys Asn Leu Asn Asn Leu Thr Gly Ile
1865                1870                1875

Thr Val Asn Asp Gly Thr Asn Gly Thr Asn Gly Ser Thr Val Ile
1880                1885                1890

Gly Lys Asp Gly Ile Ser Val Lys Asp Gly Ser Gly Asn Thr Ile
1895                1900                1905

Ala Gly Val Asp Asn Thr Ala Leu Thr Val Lys Asp Gly Ser Gly
1910                1915                1920

Asn Thr Glu Thr Ser Ile Asn Gln Ala Ile Asn Thr Leu Asn Ala
1925                1930                1935

Ala Gln Gly Glu Thr Asp Lys Phe Ala Val Lys Tyr Asp Lys Asn
1940                1945                1950

Ala Asp Gly Ser Val Asn Tyr Asn Asn Ile Thr Leu Ala Gly Thr
1955                1960                1965

Thr Ala Ser Ser Thr Gln Asp Ala Thr Thr Gly Lys Ile Thr Thr
1970                1975                1980

Thr Gly Gly Thr Ser Leu Asn Asn Val Ala Ser Ala Gly Asp Tyr
1985                1990                1995

Lys Asp Val Ala Asn Ala Ser Lys Gly Val Asn Ala Gly Asp Leu
2000                2005                2010

Asn Asn Ala Val Val Asp Ala Thr Asn Ala Ala Thr Ser Lys Gly
2015                2020                2025

Phe Ala Leu Gln Ala Ala Asp Gly Ala Lys Val Gln Lys Asn Leu
2030                2035                2040

Gly Glu Ala Val Glu Val Val Gly Ala Asp Ser Asn Ile Thr Thr
2045                2050                2055

Lys Val Ala Gly Gly Gln Val Ala Ile Glu Leu Asn Lys Asn Leu
2060                2065                2070

Asn Asn Leu Thr Gly Ile Thr Val Asn Asp Gly Thr Asn Gly Thr
2075                2080                2085

Asn Gly Ser Thr Val Ile Gly Lys Asp Gly Ile Ser Val Lys Asp
2090                2095                2100
```

```
Gly Ser Gly Asn Thr Ile Ala Gly Val Asp Asn Thr Ala Leu Thr
    2105                2110                2115

Val Lys Asp Gly Ser Gly Asn Thr Glu Thr Ser Ile Asn Gln Ala
    2120                2125                2130

Ile Asn Thr Leu Asn Ala Ala Gln Gly Glu Thr Asp Lys Phe Ala
    2135                2140                2145

Val Lys Tyr Asp Lys Asn Ala Asp Gly Ser Val Asn Tyr Asn Asn
    2150                2155                2160

Ile Thr Leu Ala Gly Thr Thr Ala Ser Ser Thr Gln Asp Ala Thr
    2165                2170                2175

Thr Gly Lys Ile Thr Thr Thr Gly Gly Thr Ser Leu Asn Asn Val
    2180                2185                2190

Ala Ser Ala Gly Asp Tyr Lys Asp Val Ala Asn Ala Ser Lys Gly
    2195                2200                2205

Val Asn Ala Gly Asp Leu Asn Asn Ala Val Val Asp Ala Thr Asn
    2210                2215                2220

Ala Ala Thr Ser Lys Gly Phe Ala Leu Gln Ala Ala Asp Gly Ala
    2225                2230                2235

Lys Val Gln Lys Asn Leu Gly Glu Ala Val Glu Val Val Gly Ala
    2240                2245                2250

Asp Ser Asn Ile Thr Thr Lys Val Ala Gly Gly Gln Val Ala Ile
    2255                2260                2265

Glu Leu Asn Lys Asn Leu Asn Asn Leu Thr Gly Ile Thr Val Asn
    2270                2275                2280

Asp Gly Thr Asn Gly Thr Asn Gly Ser Thr Val Ile Gly Lys Asp
    2285                2290                2295

Gly Ile Ser Val Lys Asp Gly Ser Gly Asn Thr Ile Ala Gly Val
    2300                2305                2310

Asp Asn Thr Ala Leu Thr Val Lys Asp Gly Ser Gly Asn Thr Glu
    2315                2320                2325

Thr Ser Ile Asn Gln Ala Ile Asn Thr Leu Asn Ala Ala Gln Gly
    2330                2335                2340

Glu Thr Asp Lys Phe Ala Val Lys Tyr Asp Lys Asn Ala Asp Gly
    2345                2350                2355

Ser Ala Asn Tyr Asn Asn Val Thr Leu Ala Gly Thr Asn Gly Thr
    2360                2365                2370

Ile Ile Ser Asn Val Lys Ala Gly Ala Val Thr Ser Thr Ser Thr
    2375                2380                2385

Asp Ala Ile Asn Gly Ser Gln Leu Tyr Gly Val Ala Asn Ser Val
    2390                2395                2400

Lys Asn Ala Ile Gly Gly Ser Thr Thr Ile Asp Ala Thr Thr Gly
    2405                2410                2415

Ala Ile Thr Thr Thr Asn Ile Gly Gly Thr Gly Ser Asn Thr Ile
    2420                2425                2430

Asp Gly Ala Ile Ser Ser Ile Lys Asp Ser Ala Thr Lys Ala Lys
    2435                2440                2445

Thr Thr Val Ser Ala Gly Asp Asn Val Val Val Thr Ser Gly Thr
    2450                2455                2460

Asn Ala Asp Gly Ser Thr Asn Tyr Glu Val Ala Thr Ala Lys Asp
    2465                2470                2475

Val Asn Phe Asp Lys Val Thr Val Gly Ser Val Val Val Asp Lys
    2480                2485                2490

Ser Ser Asn Thr Ile Lys Gly Leu Ser Asn Thr Thr Trp Asn Gly
```

-continued

```
            2495                2500                2505

Thr Ala Val Ser Gly Gln Ala Thr Glu Asp Gln Leu Lys Thr
            2510                2515                2520

Val Ser Asp Ala Gln Gly Glu Thr Asp Lys Phe Ala Val Lys Tyr
            2525                2530                2535

Asp Lys Asn Ala Asp Gly Ser Ala Asn Tyr Asn Ser Ile Thr Ala
            2540                2545                2550

Gly Asn Gly Asn Gly Thr Ala Ala Thr Ile Gly Thr Asp Thr Ala
            2555                2560                2565

Gly Asn Ser Val Val Thr Ser Gly Gly Thr Lys Ile Ser Asn Val
            2570                2575                2580

Ala Asn Gly Val Asn Ala Ser Asp Ala Val Asn Lys Gly Gln Leu
            2585                2590                2595

Asp Ser Leu Ser Thr Gly Leu Thr Asn Thr Gly Phe Gly Leu Lys
            2600                2605                2610

Ala Ala Asp Gly Asn Thr Val Asn Lys Lys Leu Gly Glu Ala Val
            2615                2620                2625

Asp Val Val Gly Ala Asp Ser Asn Ile Thr Thr Lys Val Ala Gly
            2630                2635                2640

Gly Gln Val Ala Ile Glu Leu Asn Lys Asn Leu Asn Asn Leu Thr
            2645                2650                2655

Gly Ile Thr Val Asn Asp Gly Thr Asn Gly Thr Asn Gly Ser Thr
            2660                2665                2670

Val Ile Gly Lys Asp Gly Ile Ser Ile Lys Asp Gly Ser Gly Asn
            2675                2680                2685

Thr Ile Ala Gly Val Asp Asn Thr Ala Leu Thr Val Lys Asp Ser
            2690                2695                2700

Ser Gly Asn Thr Glu Thr Ser Ile Asn Gln Ala Ile Asn Thr Leu
            2705                2710                2715

Asn Ala Ala Gln Gly Glu Thr Asp Lys Phe Ala Val Lys Tyr Asp
            2720                2725                2730

Lys Asn Ala Asp Gly Ser Val Asn Tyr Asn Asn Val Thr Leu Ala
            2735                2740                2745

Gly Thr Asn Gly Thr Ile Ile Arg Asn Val Lys Ala Gly Ala Val
            2750                2755                2760

Thr Ser Thr Ser Thr Asp Ala Ile Asn Gly Ser Gln Leu Tyr Asp
            2765                2770                2775

Ile Ala Asn Ser Val Lys Asn Ala Ile Gly Gly Ser Thr Thr Arg
            2780                2785                2790

Asp Val Thr Thr Gly Ala Ile Thr Thr Thr Asn Ile Gly Gly Thr
            2795                2800                2805

Gly Ser Asn Thr Ile Asp Gly Ala Ile Ser Ser Ile Lys Asp Ser
            2810                2815                2820

Ala Thr Lys Ala Lys Thr Thr Ile Ser Ala Gly Asp Asn Val Val
            2825                2830                2835

Val Thr Ser Gly Thr Asn Ala Asp Gly Ser Thr Asn Tyr Glu Val
            2840                2845                2850

Ala Thr Ala Lys Asp Val Asn Phe Asp Lys Val Thr Val Gly Asn
            2855                2860                2865

Val Val Val Asp Lys Ala Asn Asp Thr Ile Gln Gly Leu Ser Asn
            2870                2875                2880

Lys Asp Leu Asn Ser Thr Asp Phe Ala Thr Lys Gly Arg Ala Ala
            2885                2890                2895
```

```
Thr Glu Glu Gln Leu Lys Ala Val Ile Thr Ser Asn Ile Thr Glu
    2900                2905                2910

Val Val Asp Gly Asn Gly Asn Lys Val Asn Ile Ile Asp Gln Val
    2915                2920                2925

Val Asn Thr Lys Pro Asp Asn Lys Asn Gln Asp Ser Leu Phe Leu
    2930                2935                2940

Thr Tyr Asp Lys Gln Gly Gln Glu Thr Thr Asp Arg Leu Thr Ile
    2945                2950                2955

Gly Gln Thr Val Gln Lys Met Asn Thr Asp Gly Ile Lys Phe Phe
    2960                2965                2970

His Thr Asn Ala Asp Thr Ser Lys Gly Asp Leu Gly Thr Thr Asn
    2975                2980                2985

Asp Ser Ser Ala Gly Gly Leu Asn Ser Thr Ala Ile Gly Val Asn
    2990                2995                3000

Ala Ile Val Ala Asn Gly Ala Asp Ser Ser Val Ala Leu Gly His
    3005                3010                3015

Asn Thr Lys Val Asn Gly Lys Gln Ser Ile Ala Ile Gly Ser Gly
    3020                3025                3030

Ala Glu Ala Leu Gly Asn Gln Ser Ile Ser Ile Gly Thr Gly Asn
    3035                3040                3045

Lys Val Thr Gly Asp His Ser Gly Ala Ile Gly Asp Pro Thr Ile
    3050                3055                3060

Val Asn Gly Ala Asn Ser Tyr Ser Val Gly Asn Asn Asn Gln Val
    3065                3070                3075

Leu Thr Asp Asp Thr Phe Val Leu Gly Asn Asn Val Thr Lys Thr
    3080                3085                3090

Ile Ala Gly Ser Val Val Leu Gly Asn Gly Ser Ala Ala Thr Thr
    3095                3100                3105

Gly Ala Gly Glu Ala Gly Tyr Ala Leu Ser Val Ala Thr Asn Ala
    3110                3115                3120

Asp Lys Ala Ala Ile Thr Lys Thr Thr Ser Ser Thr Gly Ala Val
    3125                3130                3135

Ala Val Gly Asp Ala Ser Ser Gly Ile Tyr Arg Gln Ile Thr Gly
    3140                3145                3150

Val Ala Ala Gly Ser Val Asp Ser Asp Ala Val Asn Val Ala Gln
    3155                3160                3165

Leu Lys Ala Val Gly Asn Gln Val Val Thr Gln Thr Thr Leu
    3170                3175                3180

Val Asn Ser Leu Gly Gly Asn Ala Lys Val Asn Ala Asp Gly Thr
    3185                3190                3195

Ile Thr Gly Pro Thr Tyr Asn Val Ala Gln Gly Asn Gln Thr Asn
    3200                3205                3210

Val Gly Asp Ala Leu Thr Ala Leu Asp Asn Ala Ile Asn Thr Ala
    3215                3220                3225

Ala Thr Thr Ser Lys Ser Thr Val Ser Asn Gly Gln Asn Ile Val
    3230                3235                3240

Val Ser Lys Ser Lys Asn Ala Asp Gly Ser Asp Asn Tyr Glu Val
    3245                3250                3255

Ser Thr Ala Lys Asp Leu Thr Val Asp Ser Val Lys Ala Gly Asp
    3260                3265                3270

Thr Val Leu Asn Asn Ala Gly Ile Thr Ile Gly Asn Asn Ala Val
    3275                3280                3285
```

Val Leu Asn Asn Thr Gly Leu Thr Ile Ser Gly Gly Pro Ser Val
3290            3295                3300

Thr Leu Ala Gly Ile Asp Ala Gly Asn Lys Thr Ile Gln Asn Val
3305            3310                3315

Ala Asn Ala Val Asn Ala Thr Asp Ala Val Asn Lys Gly Gln Leu
3320            3325                3330

Asp Ser Ala Ile Asn Asn Val Asn Asn Asn Val Asn Glu Leu Ala
3335            3340                3345

Asn Asn Ala Val Lys Tyr Asp Asp Ala Ser Lys Asp Lys Ile Thr
3350            3355                3360

Leu Gly Gly Gly Ala Thr Gly Thr Thr Ile Thr Asn Val Lys Asp
3365            3370                3375

Gly Thr Val Ala Gln Gly Ser Lys Asp Ala Val Asn Gly Gly Gln
3380            3385                3390

Leu Trp Asn Val Gln Gln Gln Val Asp Gln Asn Thr Thr Asp Ile
3395            3400                3405

Ser Asn Ile Lys Asn Asp Ile Asn Asn Gly Thr Val Gly Leu Val
3410            3415                3420

Gln Gln Ala Gly Lys Asp Ala Pro Val Thr Val Ala Lys Asp Thr
3425            3430                3435

Gly Gly Thr Thr Val Asn Val Ala Gly Thr Asp Gly Asn Arg Val
3440            3445                3450

Val Thr Gly Val Lys Glu Gly Ala Val Asn Ala Thr Ser Lys Asp
3455            3460                3465

Ala Val Asn Gly Ser Gln Leu Asn Thr Thr Asn Gln Ala Val Val
3470            3475                3480

Asn Tyr Leu Gly Gly Gly Ala Gly Tyr Asp Asn Ile Thr Gly Ser
3485            3490                3495

Phe Thr Ala Pro Ser Tyr Thr Val Gly Asp Ser Lys Tyr Asn Asn
3500            3505                3510

Val Gly Gly Ala Ile Asp Ala Leu Asn Gln Ala Asp Gln Ala Leu
3515            3520                3525

Asn Ser Lys Ile Asp Asn Val Ser Asn Lys Leu Asp Asn Ala Phe
3530            3535                3540

Arg Ile Thr Asn Asn Arg Ile Asp Asp Val Glu Lys Lys Ala Asn
3545            3550                3555

Ala Gly Ile Ala Ala Ala Met Ala Leu Glu Ser Ala Pro Tyr Val
3560            3565                3570

Pro Gly Lys Tyr Thr Tyr Ala Ala Gly Ala Ala Tyr His Gly Gly
3575            3580                3585

Glu Asn Ala Val Gly Val Thr Leu Arg Lys Thr Ala Asp Asn Gly
3590            3595                3600

Arg Trp Ser Ile Thr Gly Gly Val Ala Ala Ala Ser Gln Gly Asp
3605            3610                3615

Ala Ser Val Arg Ile Gly Ile Ser Gly Val Ile Asp
3620            3625                3630

<210> SEQ ID NO 3
<211> LENGTH: 795
<212> TYPE: DNA
<213> ORGANISM: Acinetobacter sp

<400> SEQUENCE: 3
atgaaagcat taacaaaaa aattatgttt ggtgtattca gcggtcttgt gatgtcattg      60

-continued

```
agccatgctg ctgaagtcga aagtgcaaat acgcaagaaa tccattttcc tgaaatcaaa      120
gacagctatt taaaacaagt gaaccgttat gaatatgacg atgtcgcacg tttagacaag      180
ggattaacca aagatcagat tcgccatatt ttgggaaatc ctcaattctc tgaaggtctt      240
tttgcggtta agacatggaa ttatgtattg gatattcgtg agcctaactc aaaccaatat      300
aagcgttgcc aattacgcat agattttgat aagcaatacc gttcagacaa tctatattgg      360
aaaggtgaac aatgccaagg cttaatggct tggggattaa taatcagtc tgagactgag       420
caaacgactc tagcacctgg tgggcagtct gcaagtgttt tgttttattt tgatcatgcg      480
gataaaaatg gtgtaaagaa cgctgaagtg attcgtaaaa tcgcagatca gattaaacaa      540
tctgatgcga atagccctgt ttttgtggct ggatatactg atcgtttagg atcatttcag      600
tataaccaac gttatctgc ccaaagagcg aatacagtcg ttgaactctt gaagcaacaa       660
ggcattcgtg gcgagcaaat tcagtacagt gctgaaaata aaacagatgt gtaccaaaag      720
tgcgcaggga tcaataaaaa gatccaactg gttgaatgtc tagcacctaa ccgtcgtgtg      780
aatatcacgt ggtaa                                                       795
```

<210> SEQ ID NO 4
<211> LENGTH: 264
<212> TYPE: PRT
<213> ORGANISM: Acinetobacter sp

<400> SEQUENCE: 4

Met Lys Ala Phe Asn Lys Lys Ile Met Phe Gly Val Phe Ser Gly Leu
1               5                   10                  15

Val Met Ser Leu Ser His Ala Ala Glu Val Glu Ser Ala Asn Thr Gln
            20                  25                  30

Glu Ile His Phe Pro Glu Ile Lys Asp Ser Tyr Leu Lys Gln Val Asn
        35                  40                  45

Arg Tyr Glu Tyr Asp Asp Val Ala Arg Leu Asp Lys Gly Leu Thr Lys
    50                  55                  60

Asp Gln Ile Arg His Ile Leu Gly Asn Pro Gln Phe Ser Glu Gly Leu
65                  70                  75                  80

Phe Ala Val Lys Thr Trp Asn Tyr Val Leu Asp Ile Arg Glu Pro Asn
                85                  90                  95

Ser Asn Gln Tyr Lys Arg Cys Gln Leu Arg Ile Asp Phe Asp Lys Gln
            100                 105                 110

Tyr Arg Ser Asp Asn Leu Tyr Trp Lys Gly Glu Gln Cys Gln Gly Leu
        115                 120                 125

Met Ala Trp Gly Ile Asn Asn Gln Ser Glu Thr Glu Gln Thr Thr Leu
    130                 135                 140

Ala Pro Gly Gly Gln Ser Ala Ser Val Leu Phe Tyr Phe Asp His Ala
145                 150                 155                 160

Asp Lys Asn Gly Val Lys Asn Ala Glu Val Ile Arg Lys Ile Ala Asp
                165                 170                 175

Gln Ile Lys Gln Ser Asp Ala Asn Ser Pro Val Phe Val Ala Gly Tyr
            180                 185                 190

Thr Asp Arg Leu Gly Ser Phe Gln Tyr Asn Gln Arg Leu Ser Ala Gln
        195                 200                 205

Arg Ala Asn Thr Val Val Glu Leu Leu Lys Gln Gln Gly Ile Arg Gly
    210                 215                 220

Glu Gln Ile Gln Tyr Ser Ala Glu Asn Lys Thr Asp Val Tyr Gln Lys
225                 230                 235                 240

```
Cys Ala Gly Ile Asn Lys Lys Ile Gln Leu Val Glu Cys Leu Ala Pro
            245                 250                 255

Asn Arg Arg Val Asn Ile Thr Trp
         260

<210> SEQ ID NO 5
<211> LENGTH: 11858
<212> TYPE: DNA
<213> ORGANISM: Acinetobacter sp

<400> SEQUENCE: 5
ttgctttaat tgtatgtaaa ttgttaaata aaaaaaattg tacattttat atgcattgct      60
aaagcagaac ctactgccca aaatgcatct cctaaggaaa agcgatatga ataaaatcta     120
caaagtgatt tggaatgcga ctttgttggc atgggttgca gtatctgaat tggcaaaagg     180
gaaaaccaaa tctacgacat caaaatccaa agctaaatca ttatcttcat ctgtaatagt     240
tggtgggata atattaacaa caccttttatc tttaatagca gctactgttc aagttggagg     300
gggaactaat tctggaacaa ctgctacagc ttctacgaat tgtgcagact tatataatta     360
tcaaaatcct gagaactcag gctctggagc ggctgggaat tataatgcag gaaatccaag     420
tgtgtgttcg atcgctatag gtgaaaacgc acaaggtggt acttctggaa ctggagggtc     480
gccagggata gcgataggtg gaaattctaa agctacgggt ggtttatctg ttgctatagg     540
cggatatgct caagcgacaa atgttggaag tattgcttta ggcacagcag ctttatcaag     600
tggttttaac agtttagcaa tatccagaca agctgctgca acgaataact attcaatagc     660
tataggtaca acttcagttt cgaaaggagt tggatcgatt gctatggggc attcaacgaa     720
tgcttctgga gatcaatcga tagcaattgg tagctcggat gctgttaatt cagcaacagc     780
aacaacaaca tacgatggta caacaaatac tcaagcatca ggtagtaaat cgattgctat     840
aggtgcaagc gcaaaggcat caaccaataa cagcattgca ctaggtgcag atcggtaac     900 ttctgcacaa tctggtaatt cttatcttac tggtgtaggt gcatcagcta caaatggtgt     960
tgtatctgtt ggaacttcaa ctgcaacacg tcgtatccaa aatgtagcag atggttcagc    1020
cgcttcagat gctgtgacag ttgctcagtt ggataaagct tatgatgata caaatggtcg    1080
tttagctgct gctttaggta caggtagtgg tgctgcctat aatgcagcaa acaatacata    1140
taccgctcca acgaatattg ggggaacagg taaaaatacg attgatgatg caattaaagc    1200
aactcaacga agtgtagtcg ctggatcaaa tattgtcgtt accccgacga cagcttctga    1260
tggttcaata tcgtattcgg ttgctacaag cgcaacaccg acgtttacaa gtataactgt    1320
aaacaatgca ccaacggcag gtacagatgc gaccaacaag acttatgtag actcaaaagc    1380
agcagcatcg agaacagaag tagcagctgg aagcaatgta tctggtgtag taaaaacgac    1440
aggcgcaaac ggtcaagacg tttatacagt aaatgccaat ggtacgactg catcagcagg    1500
ttcttcagca gttaccgtaa caccaggcac gaaagatgca aataatgtca ctgactataa    1560
agtagactta tcagcgacta caaaaaccga tatccaaaaa ggtgtagatg caaaaaatgc    1620
tgtagatacc gcaggtctaa aatttaaagg tgatacagca accacaagca ataccaagaa    1680
attaggtgac accgtttcga ttacgggtga tacgaacatt agtacagttg cgacaacaga    1740
tggtgtacag gttaagttaa atccaaactt ggatttagga gcaactggta gcgttaaaac    1800
gggtaatacc acgattaaca atgcaggtgt aacagctgat caagttacgg ttggtggtgt    1860
tgttattaac aacacatcag gtattaatgc tggtggtaaa gcgattacta atgtagcagc    1920
accaacaaat aacacagatg ctgctaacaa gaagtatgta gatgatgcag gtacagcatt    1980
```

```
aaccaatttg ggctttggat taaaagcaca agatggtacg actgtgaaca agaaattagg    2040
tgaagcagtt gatattgttg gttcaaacag caacatcagt acaaaagtaa atgcaggcaa    2100
agtagaagtt gcactatcca atacattgga cttaggtact acaggtagcg ttactacggg    2160
ttcaactgta attaacaatg ctggtgttac ggcaactcaa gttaccgcaa acaaagtcac    2220
aataaacaat gcaccaacag caggtacaga tgcgaccaac aagacttatg tagactcaaa    2280
agcagcagca tcaagaacag aagtcgcagc tggaagcaat gtatctggtg tagtaaaaac    2340
gacaggcgca aacggtcaag atatttatgc agtaaatgcc aatggtacga ctgcatcagc    2400
aggttcttca gcagttaccg taacaccagg cacgaaagat gcaaataatg tcactgacta    2460
taaagtagac ttgtcagcga ctacaaaaac cgatattcaa aaggtgtag atgcaaaaaa    2520 tgctgtagat actgcaggtc taaaatttaa aggtgataca gcaaccacaa gcaataccaa    2580
gaaattaggt gacaccgttt cgattacggg tgatacgaac attagtacag ttgcaacaac    2640
tgatggtgta caggttaagt taaatccaaa cttagattta ggagcaactg gtagcgttaa    2700
aacgggtaat accacgatta acaatgcagg tgtaacagct gaccaagtta cggttggtgg    2760
tgttgttatt aacaacacat caggtattaa tgctggtggt aaagcgatta ccaatgtagc    2820
agcaccaaca aataacacag atgctgctaa caagaagtat gtagatgacg caggtacagc    2880
attaaccaat ttgggctttg gattaaaagc gcaagatggt acgactgtga acaagaaatt    2940
aggtgaagca gttgatattg ttggttcaaa cagcaacatc agtacaaaag taaatgcagg    3000
caaagtagaa gttgcactat ccaatacatt ggacttaggt actacaggta gcgttactac    3060
gggttcaact gtaattaaca atgctggtgt tacggcaact caagttaccg caaacaaagt    3120
cacagttaat aatgcaccaa cagcaggtac agatgcgacc aataaaactt atgtagactc    3180
aaaagcagcg gcatcaagaa cagaagtcgc agctggaagc aatgtatctg gcgtagtaaa    3240
aacgacaggt gcaaacggtc aagacgttta tacagtaaat gccaatggta cgactgcatc    3300
agcaggttct tcagcagtta ccgtaacacc aggcacgaaa gatgcaaata atgtcactga    3360
ctataaagta gacttgtcag cgactacaaa aaccgatatt caaaaggtg tagatgcaaa    3420 aaatgctgta gataccgcag gtctaaaatt taaaggtgat acagcaacca caagcaatac    3480
caagaaatta ggtgacaccg tttcgattac gggtgatacg aacattagta cagttgcgac    3540
aactgatggt gtacaggtta agctaaatcc aaacttggat ttaggagcaa ctggtagcgt    3600
taaaacgggt aataccacga ttaacaatgc aggtgtaaca gctgatcaag ttacagttgg    3660
tggtgttgtt attaacaaca catcaggtat taatgctggt ggtaaagcga ttaccaatgt    3720
agcagcacca caaataaca cagatgctgc taacaagaag tatgtagatg atgcaggtac    3780
agcattaacc aatttgggct ttggattaaa agcgcaagat ggtacgactg tgaacaagaa    3840
attaggcgaa gcagttgaag ttgttggtgc ggacagtaac atcaccacga agttgcagg    3900 cggtcaggtt gcaattgagt taaataaaaa cctcaacaac ttaactggca ttaccgtgaa    3960
cgatggaacc aatggcacca atggttcaac tgtgattggt aaagatggta tttcggttaa    4020
agatggttca ggcaatacca ttgcaggtgt agataacaca gcgttgacag ttaaagatgg    4080
cagtggcaac acagaaacca gcattaacca agcgatcaac acgttaaatg cagcgcaagg    4140
tgaaactgat aagtttgcag tgaagtacga caaaaatgct gatggcagtg tgaactacaa    4200
caacatcaca ttgcaggta cgactgcaag cagtacacaa gatgcaacta caggcaagat    4260
caccacaaca ggtggaacaa gcttgaacaa tgttgcaagt gcgggtgact acaaagatgt    4320
```

```
tgccaatgca agcaaaggtg taaacgcagg tgacttaaac aatgcagttg ttgatgcaac    4380
caatgcagca accagcaaag gctttgcatt acaagcagca gatggcgcta aagttcagaa    4440
gaacctaggc gaagcagttg aagttgtcgg tgccgacagc aacatcacca caaaagttgc    4500
aggcggtcag gttgcaattg agttaaataa aaacctcaac aacttaactg gcattaccgt    4560
gaacgatgga accaatggca ccaatggttc aactgtgatt ggtaaagatg gtatttcagt    4620
taaagacggt tcaggcaata ccattgcagg tgtagataac acagcgttga cagttaaaga    4680
tggcagtggc aacacagaaa ccagcattaa ccaagcgatc aacacgttaa atgcagcgca    4740
aggtgaaact gataagtttg cagtgaagta cgacaaaaat acggatggta gtaccaacta    4800
caacagtatt actgcaggca atggtaacgg tactgcagca acgatcggaa ctgacacagc    4860
aggtaatagt gttgtgacca gtggcggaac taaaattagt aatgttgcga atggtgtcaa    4920
tgcaagtgat gcagtaaaca aaggtcaatt ggatagctta agtacaggtc ttaccaatac    4980
aggctttggt ttaaaagcag cagatggcaa caccgttaac aaaaaattag gcgaagcagt    5040
agacgttgtc ggtgctgaca gcaacatcac cacgaaagtt gcaggcggtc aggttgcgat    5100
tgagttaaat aaaaacctca acaacttaac tggcattacc gtgaacgatg gaaccaatgg    5160
caccaatggt tcaactgtga ttggtaaaga tggtatttcg attaaagatg gttcaggcaa    5220
taccattgca ggtgtagata acacagcgtt gacagttaaa gatggcagtg gcaacacaga    5280
aaccagcatt aaccaagcga tcaacacgtt aaatgcagcg caaggtgaaa ctgacaagtt    5340
tgcagtgaag tacgacaaga atgctgatgg cagtgcaaac tacaacaaca tcacattggc    5400
aggtacgact gcaagtagca cgcaagatgc aacaacaggc aagatcacca caacaggtgg    5460
aacaagcttg aacaacgttg caagtgcagg tgactacaaa gatgttgcca atgcaagcaa    5520
aggtgtaaac gcaggtgact tgaacaatgc agttgttgat gcaaccaatg cagcaaccag    5580
caaaggcttt gcattacaag cagcagatgg cgctaaagtt cagaagaacc taggcgaagc    5640
agttgaagtt gtcggtgcgg acagcaacat caccacaaaa gtagtgggtg acaagttgc    5700 gattgagtta aataaaaacc tcaacaactt aactggcatt accgtgaacg atggaaccaa    5760
tggcacaaat ggttcaactg tgattggtaa agatggtatt tcggttaaag atggttcagg    5820
taataccatt gcaggtgtag ataacacagc gttgacagtt aaagatggca gtggcaacac    5880
agaaaccagc attaaccaag cgatcaacac gttaaatgca gcgcaaggtg aaactgataa    5940
gtttgcagtg aagtacgaca aaaatgctga tggcagtgtg aactacaaca acatcacatt    6000
ggcaggtacg actgcaagca gtacacaaga tgcaactaca ggcaagatca ccacaacagg    6060
tggaacaagc ttgaacaatg ttgcaagtgc gggtgactac aaagatgttg ccaatgcaag    6120
caaaggtgta aacgcaggtg acttaaacaa tgcagttgtt gatgcaacca atgcagcaac    6180
cagcaaaggc tttgcattac aagcagcaga tggcgctaaa gttcagaaga acctaggcga    6240
agcagttgaa gttgtcggtg ccgacagcaa catcaccaca aaagttgcag gcggtcaggt    6300
tgcaattgag ttaaataaaa acctcaacaa cttaactggc attaccgtga acgatggaac    6360
caatggcacc aatggttcaa ctgtgattgg taaagatggt atttcagtta agacggttc    6420 aggcaatacc attgcaggtg tagataacac agcgttgaca gttaaagatg gcagtggcaa    6480
cacagaaacc agcattaacc aagcgatcaa cacgttaaat gcagcgcaag gtgaaactga    6540
taagtttgca gtgaagtacg acaaaaatgc tgatggcagt gtgaactaca acaacatcac    6600
attggcaggt acgactgcaa gcagtacaca agatgcaact acaggcaaga tcaccacaac    6660
aggtggtaca agcttgaaca atgttgcaag tgcgggtgac tacaaagatg ttgccaatgc    6720
```

```
aagcaaaggt gtaaacgcag gtgacttgaa caatgcagtt gttgatgcaa ccaatgcagc    6780
gaccagcaaa ggctttgcat tacaagcagc agatggcgct aaagttcaga agaacctagg    6840
cgaagcagtt gaagttgttg gtgcggacag taacatcacc acgaaagttg caggcggtca    6900
ggttgcaatt gagttaaata aaaacctcaa caacttaact ggcattaccg tgaacgatgg    6960
aaccaatggc accaatggtt caactgtgat tggtaaagat ggtatttcgg ttaaagatgg    7020
ttcaggcaat accattgcag gtgtagataa cacagcgttg acagttaaag atggcagtgg    7080
caacacagaa accagcatta accaagcgat caacacgtta aatgcagcgc aaggtgaaac    7140
tgataagttt gcagtgaagt acgacaaaaa tgctgatggc agtgcaaact ataacaatgt    7200
cactttagct ggtacaaatg gcacaataat cagcaatgtt aaagcgggtg ctgtgacctc    7260
aacatctact gatgcgatca atggtagcca attatatggt gttgcaaaca gcgtgaagaa    7320
tgcaattggt ggttcaacca caattgatgc aacgactggt gcaatcacga cgaccaatat    7380
tggtggtaca ggttcaaata cgattgatgg tgcaatcagc agtattaaag attcagcgac    7440
taaagcgaaa accacggtaa gtgctgggga taatgttgtc gttacatcgg taccaatgc    7500 agatggctca acaaactatg aagttgcgac agcgaaagac gttaactttg acaaagtgac    7560
tgtaggtagt gttgttgtag ataaatcaag caatacaatc aaaggattaa gtaataccac    7620
ttggaacgga acagcagtat caggtcaagc ggcgacagaa gaccagttaa aaacggtcag    7680
cgatgcgcaa ggtgaaactg ataagtttgc agtgaagtac gacaaaaatg ctgatggcag    7740
tgcgaactac aacagtatta ctgcaggcaa tggtaacggt actgcagcaa cgatcggaac    7800
tgacacagca ggtaatagtg ttgtgaccag tggcggaact aaaattagta atgttgcgaa    7860
tggtgtcaat gcaagtgatg cagtaaacaa aggtcaattg gatagcttaa gtacaggtct    7920
taccaataca ggctttggtt taaaagcagc agatggcaac accgttaaca aaaaattagg    7980
cgaagcagta gacgttgtcg gtgctgacag caacatcacc acgaaagttg caggcggtca    8040
ggttgcgatt gagttaaata aaaacctcaa caacttaact ggcattaccg tgaacgatgg    8100
aaccaatggc accaatggtt caactgtgat tggtaaagat ggtatttcga ttaaagatgg    8160
ttcaggcaat accattgcag gtgtagataa cacagcgttg acggttaaag atagcagtgg    8220
caacacagaa accagcatta accaagcgat caacacgtta aatgcagcgc aaggtgaaac    8280
tgataagttt gcagtgaagt acgataagaa tgctgatggc agtgtgaact ataacaatgt    8340
cactttagca ggtacaaatg gcacaataat cagaaatgtt aaagcgggtg ctgtgacctc    8400
aacatctact gatgcgatca atggtagcca attatacggt attgcaaaca gcgtgaagaa    8460
tgcaattggt ggttcaacca caagagatgt aacgactggt gcaatcacaa cgaccaatat    8520
tggtggtaca ggttcaaaca cgattgatgg tgcaatcagc agtattaaag attcagcgac    8580
taaagcgaaa accacgataa gtgctgggga taatgttgtc gttacatcgg taccaatgc    8640 agatggctca acaaactatg aagttgcgac agcgaaagac gttaactttg acaaagtaac    8700
tgtaggtaat gttgttgttg ataaggcaaa tgacacgatc caaggtttga gcaataaaga    8760
tctaaattca actgattttg cgaccaaagg tagagctgcg actgaagaac agttaaaagc    8820
agtgattacc agtaatatca cggaagttgt ggatggtaat ggcaacaagg tgaatattat    8880
tgaccaagtt gtaaatacca aacctgacaa taagaaccaa gattcattgt tcttaacgta    8940
tgacaaacaa ggtcaagaaa ccacagatcg cctaacgatt ggtcaaacgg tacagaagat    9000
gaatactgat ggtattaaat tcttccatac caatgccgat acatcaaaag gtgatttggg    9060
```

```
tacaacaaat gactcaagtg caggtggttt aaactctaca gcaattggtg taaatgcgat    9120
tgttgcgaat ggtgcagata gttcagttgc tttaggtcat aacaccaaag tcaatggtaa    9180
acaatcaatt gcaattggtt ctggtgcaga agctttaggc aatcaatcga tcagtattgg    9240
tacaggcaat aaagtcactg gtgatcattc gggtgcgatt ggtgatccaa ctattgtaaa    9300
tggtgcaaac agctactctg tgggtaataa caaccaagta cttacagatg cactttcgt    9360 acttggaaac aatgtcacca aaactattgc tggttcagta gtattgggta acggttcagc    9420
tgcaacgaca ggtgctggtg aggcaggcta tgccttatct gtagcaacaa atgcagataa    9480
agccgcgatc actaaaacta cgtcaagcac tggtgctgtt gcagttggtg atgcgtcgag    9540
cggtatttat cgtcaaatta ccggtgttgc tgcgggtagc gtagattcag atgctgtgaa    9600
cgttgcacag ttaaaagcgg tgggtaacca agttgtaacg actcaaacta cattggtgaa    9660
cagtttgggt ggtaacgcta agtaaatgc agacggtacg attacaggac caacttataa    9720
tgttgctcaa ggtaatcaga ccaatgttgg tgatgcatta actgcgcttg ataacgcaat    9780
taatactgcg gcaacaacat ctaaatcgac tgtttctaat ggtcagaata ttgttgtcag    9840
caagagcaaa aatgcagatg gttcagacaa ctatgaagta tcaacagcaa aagacttgac    9900
agttgattct gtcaaagcgg gtgatacggt tctgaataat gcaggtatta caattggcaa    9960
taacgcagtt gtattgaaca acactggatt aaccattagt ggtggaccaa gtgttacctt    10020
ggcaggcatc gatgcaggca ataaaaccat tcaaaatgtt gcgaatgcag taaatgcaac    10080
agatgcagtc aacaaagggc aattggacag cgcaattaac aatgtgaata acaatgtaaa    10140
tgagcttgcc aacaacgctg ttaaatatga cgatgcatca aaagataaga tcacacttgg    10200
tggtggggca actggtacaa caatcaccaa tgtgaaagat ggtactgttg cgcaaggttc    10260
taaagatgct gtgaatggcg gtcaattgtg gaatgttcaa caacaagttg atcagaacac    10320
aactgatatt agcaatatca aaaatgatat taacaacggt actgttggtt tggttcaaca    10380
agcaggtaaa gatgcaccag tgacggttgc aaaagatact ggcggtacaa cggtgaatgt    10440
cgctggaaca gatggcaacc gagtagtgac aggtgttaag gaaggtgcag tgaatgcaac    10500
atctaaagat gctgtcaatg gtagtcaatt gaatacaacc aaccaagcgg tagtcaatta    10560
tcttggtggt ggggcaggtt atgacaacat tacaggtagc ttcacagcgc caagttatac    10620
ggtaggtgac tcgaaataca acaatgttgg tgcgcaatt gatgcattga atcaagcaga    10680
tcaagcattg aatagcaaaa ttgacaatgt cagtaacaag ttggataacg cattccgtat    10740
taccaacaac cgtattgatg atgtagagaa aaaagccaat gctggtattg ccgctgcgat    10800
ggctctggaa tcagcaccat atgtcccagg taaatatacc tatgcagcag cgcagctta    10860 ccacggtggt gaaaatgcgg taggtgtgac ttttacgtaaa actgcagaca atggtcgttg    10920
gtcgattaca ggcggtgtag ctgcagcgtc tcaaggcgat gcaagtgttc gtatcggtat    10980
cagcggtgtg attgactaat tcactcgaca gggaagatct tcgggtcttc cttttctc    11040 gaaattttt aagagagaa aaaatgaaag catttaacaa aaaaattatg tttggtgtat    11100
tcagcggtct tgtgatgtca ttgagccatg ctgctgaagt cgaaagtgca aatacgcaag    11160
aaatccattt tcctgaaatc aaagacagct atttaaaaca agtgaaccgt tatgaatatg    11220
acgatgtcgc acgtttagac aagggattaa ccaaagatca gattcgccat attttgggaa    11280
atcctcaatt ctctgaaggt cttttgcgg ttaagacatg gaattatgta ttggatattc    11340
gtgagcctaa ctcaaaccaa tataagcgtt gccaattacg catagatttt gataagcaat    11400
accgttcaga caatctatat tggaaaggtg aacaatgcca aggcttaatg gcttggggga    11460
```

-continued

```
ttaataatca gtctgagact gagcaaacga ctctagcacc tggtgggcag tctgcaagtg      11520
ttttgtttta ttttgatcat gcggataaaa atggtgtaaa gaacgctgaa gtgattcgta      11580
aaatcgcaga tcagattaaa caatctgatg cgaatagccc tgttttgtg gctggatata       11640 ctgatcgttt aggatcattt cagtataacc aacgtttatc tgcccaaaga gcgaatacag      11700
tcgttgaact cttgaagcaa caaggcattc gtggcgagca aattcagtac agtgctgaaa      11760
ataaaacaga tgtgtaccaa aagtgcgcag ggatcaataa aaagatccaa ctggttgaat      11820
gtctagcacc taaccgtcgt gtgaatatca cgtggtaa                              11858
```

<210> SEQ ID NO 6
<211> LENGTH: 21
<212> TYPE: DNA
<213> ORGANISM: Acinetobacter sp

<400> SEQUENCE: 6
gttttcccag tcacgacgtt g                                                21

<210> SEQ ID NO 7
<211> LENGTH: 29
<212> TYPE: DNA
<213> ORGANISM: Artificial Sequence
<220> FEATURE:
<223> OTHER INFORMATION: Primer

<400> SEQUENCE: 7
ggtttgagca ataaagatct aaattcaac                                        29

<210> SEQ ID NO 8
<211> LENGTH: 48
<212> TYPE: DNA
<213> ORGANISM: Artificial Sequence
<220> FEATURE:
<223> OTHER INFORMATION: Primer

<400> SEQUENCE: 8
gggtccctga agaggactt caagcccacc accaagataa ttgactac                    48

<210> SEQ ID NO 9
<211> LENGTH: 25
<212> TYPE: DNA
<213> ORGANISM: Artificial Sequence
<220> FEATURE:
<223> OTHER INFORMATION: Primer

<400> SEQUENCE: 9
tgggtctaga gaattagtca atcac                                            25

<210> SEQ ID NO 10
<211> LENGTH: 48
<212> TYPE: DNA
<213> ORGANISM: Artificial Sequence
<220> FEATURE:
<223> OTHER INFORMATION: Primer

<400> SEQUENCE: 10
cttgaagtcc tctttcaggg acccggtggt ggggcaggtt atgacaac                   48

<210> SEQ ID NO 11
<211> LENGTH: 8
<212> TYPE: PRT
<213> ORGANISM: Artificial Sequence
<220> FEATURE:

-continued

```
<223> OTHER INFORMATION: HRV 3C protease recognition site

<400> SEQUENCE: 11

Leu Glu Val Leu Phe Gln Gly Pro
1               5

<210> SEQ ID NO 12
<211> LENGTH: 169
<212> TYPE: PRT
<213> ORGANISM: Acinetobacter sp

<400> SEQUENCE: 12

Ser Gln Leu Asn Thr Thr Asn Gln Ala Val Val Asn Tyr Leu Gly Gly
1               5                   10                  15

Gly Leu Glu Val Leu Phe Gln Gly Pro Gly Gly Gly Ala Gly Tyr Asp
                20                  25                  30

Asn Ile Thr Gly Ser Phe Thr Ala Pro Ser Tyr Thr Val Gly Asp Ser
            35                  40                  45

Lys Tyr Asn Asn Val Gly Gly Ala Ile Asp Ala Leu Asn Gln Ala Asp
    50                  55                  60

Gln Ala Leu Asn Ser Lys Ile Asp Asn Val Ser Asn Lys Leu Asp Asn
65                  70                  75                  80

Ala Phe Arg Ile Thr Asn Asn Arg Ile Asp Asp Val Glu Lys Lys Ala
                85                  90                  95

Asn Ala Gly Ile Ala Ala Ala Met Ala Leu Glu Ser Ala Pro Tyr Val
            100                 105                 110

Pro Gly Lys Tyr Thr Tyr Ala Ala Gly Ala Ala Tyr His Gly Gly Glu
        115                 120                 125

Asn Ala Val Gly Val Thr Leu Arg Lys Thr Ala Asp Asn Gly Arg Trp
    130                 135                 140

Ser Ile Thr Gly Gly Val Ala Ala Ala Ser Gln Gly Asp Ala Ser Val
145                 150                 155                 160

Arg Ile Gly Ile Ser Gly Val Ile Asp
                165
```